US007678784B2

(12) United States Patent
Wu et al.

(10) Patent No.: US 7,678,784 B2
(45) Date of Patent: Mar. 16, 2010

(54) OXIME-CONTAINING MACROCYCLIC ACYL GUANIDINES AS β-SECRETASE INHIBITORS

(75) Inventors: Yong-Jin Wu, Madison, CT (US);
Samuel Gerritz, Guilford, CT (US);
Shuhao Shi, Madison, CT (US);
Shirong Zhu, Cheshire, CT (US)

(73) Assignee: Bristol-Myers Squibb Company, Princeton, NY (US)

( * ) Notice: Subject to any disclaimer, the term of this patent is extended or adjusted under 35 U.S.C. 154(b) by 195 days.

(21) Appl. No.: 11/940,597

(22) Filed: Nov. 15, 2007

(65) Prior Publication Data
US 2008/0139523 A1  Jun. 12, 2008

Related U.S. Application Data

(60) Provisional application No. 60/860,123, filed on Nov. 20, 2006.

(51) Int. Cl.
*C07D 267/22* (2006.01)
*C07D 225/04* (2006.01)
*A61K 31/33* (2006.01)

(52) U.S. Cl. ...................... 514/183; 540/456
(58) Field of Classification Search ................. 540/456; 514/183
See application file for complete search history.

(56) References Cited

FOREIGN PATENT DOCUMENTS

| WO | WO 02/100856 | 12/2002 |
|---|---|---|
| WO | WO 2004/062625 | 7/2004 |
| WO | WO 2005/018545 | 3/2005 |
| WO | WO 2005/049585 | 6/2005 |

OTHER PUBLICATIONS

Cole, D.C. et al., "Acylguanidines as Small-Molecule β-Secretase Inhibitors", Journal of Medicinal Chemistry, vol. 49, No. 21, pp. 6158-6161 (2006).
Ghosh, A.K. et al., "Structure-based design of cycloamide-urethane-derived novel inhibitors of human brain memapsin 2 (β-secretase)", Bioorganic & Medicinal Chemistry Letters, vol. 15, pp. 15-20 (2005).
Hussain, I. et al., "Identification of a Novel Aspartic Protease (Asp 2) as β-Secretase", Molecular and Cellular Neuroscience, vol. 14, pp. 419-427 (1999).
Lin, X. et al., "Human aspartic protease memapsin 2 cleaves the β-secretase site of β-amyloid percursor protein", Proceedings of the National Academy of Sciences, vol. 97, No. 4, pp. 1456-1460 (2000).
Luo, Y. et al., "Mice deficient in BACE1, the Alzheimer's β-secretase, have normal phenotype and abolished β-amyloid generation", Nature Neuroscience, vol. 4, No. 3, pp. 231-232 (2001).
Roberds, S.L. et al., "BACE knockout mice are healthy despite lacking the primary β-secretase activity in brain: implications for Alzheimer's disease therapeutics", Human Molecular Genetics, vol. 10, No. 12, pp. 1317-1324 (2001).
Seiffert, D. et al., "Presenilin-1 and -2 are Molecular Targets for γ-Secretase Inhibitors", The Journal of Biological Chemistry, vol. 275, No. 44, pp. 34086-34091 (2000).
Selkoe, D.J., "Alzheimer's Disease: Genes, Proteins, and Therapy", Physiological Reviews, vol. 81, No. 2, pp. 741-766 (2001).
Selkoe, D.J., "Cell Biology of the Amyloid β-Protein Precursor and the Mechanism of Alzheimer's Disease", Annu. Rev. Cell Biol., vol. 10, pp. 373-403 (1994).
Sinha, S. et al., "Purification and cloning of amyloid precursor protein β-secretase from human brain", Nature, vol. 402, pp. 537-540 (1999).
Stachel, S.J. et al., "Macrocyclic Inhibitors of β-Secretase: Functional Activity in an Animal Model", Journal of Medicinal Chemistry, vol. 49, No. 21, pp. 6147-6150 (2006).
Thal, D.R. et al., "Two Types of Sporadic Cerebral Amyloid Angiopathy", Journal of Neuropathology and Experimental Neurology, vol. 61, No. 3, pp. 282-293 (2002).
Vassar, R. et al., "β-Secretase Cleavage of Alzheimer's Amyloid Precursor Protein by the Transmembrane Aspartic Protease BACE", Science, vol. 286, pp. 735-741 (1999).
Walsh, D.M. et al., "Amyloid-β oligomers: their production, toxicity and therapeutic inhibition", Biochemical Society Transactions, vol. 30, Pt. 4, pp. 552-557 (2002).
Wolfe, M.S., "Secretase Targets for Alzheimer's Disease: Identification and Therapeutic Potential", vol. 44, No. 13, pp. 2039-2060 (2001).
Yan, R. et al., "Membrane-anchored aspartyl protease with Alzheimer's disease β-secretase activity", Nature, vol. 402, pp. 533-537 (1999).

*Primary Examiner*—Bruck Kifle
(74) *Attorney, Agent, or Firm*—John F. Levis; Aldo A. Algieri

(57) ABSTRACT

There is provided a series of oxime-containing macrocyclic acyl guanidines of Formula (I) or a stereoisomer; or a pharmaceutically acceptable salt thereof wherein $R_1$, $R_2$, $R_3$, $R_4$, n and X as defined herein, their pharmaceutical compositions and methods of use. These novel compounds inhibit the processing of amyloid precursor protein (APP) by β-secretase and, more specifically, inhibit the production of Aβ-peptide. The present disclosure is directed to compounds useful in the treatment of neurological disorders related to β-amyloid production, such as Alzheimer's disease and other conditions affected by anti-amyloid activity.

8 Claims, No Drawings

US 7,678,784 B2

OXIME-CONTAINING MACROCYCLIC ACYL GUANIDINES AS β-SECRETASE INHIBITORS

CROSS-REFERENCE TO RELATED APPLICATIONS

This is a non-provisional application which claims the benefit of U.S. Provisional Application No. 60/860,123 filed Nov. 20, 2006.

FIELD OF THE DISCLOSURE

This patent application provides oxime-containing macrocyclic acyl guanidines compounds having drug and bio-affecting properties, their pharmaceutical compositions and method of use. In particular, the disclosure is concerned with a series of novel oxime-containing macrocyclic acyl guanidines which are inhibitors of the β-amyloid peptide (β-AP) production, thereby acting to prevent the accumulation of amyloid protein deposits in the brain and, therefore, are useful in the treatment of neurological disorders related to β-amyloid production. More particularly, the present disclosure relates to the treatment of Alzheimer's Disease (AD) and similar diseases.

BACKGROUND

Alzheimer's Disease is a progressive, neurodegenerative disorder characterized by memory impairment and cognitive dysfunction. AD is characterized pathologically by the accumulation of senile (neuritic) plaques, neurofibrillary tangles, amyloid deposition in neural tissues and vessels, synaptic loss, and neuronal death. It is the most common form of dementia and it now represents the third leading cause of death after cardiovascular disorders and cancer. The cost of Alzheimer's Disease is enormous (in the U.S., greater than $100 billion annually) and includes the suffering of the patients, the suffering of families, and the lost productivity of patients and caregivers. As the longevity of society increases, the occurrence of AD will markedly increase. It is estimated that more than 10 million Americans will suffer from AD by the year 2020, if methods for prevention and treatment are not found. Currently, AD is estimated to afflict 10% of the population over age 65 and up to 50% of those over the age of 85. No treatment that effectively prevents AD or reverses the clinical symptoms and underlying pathophysiology is currently available (for review see Selkoe, D. J. *Ann. Rev. Cell Biol.* 1994, 10, 373-403).

Histopathological examination of brain tissue derived upon autopsy or from neurosurgical specimens in affected individuals reveals the occurrence of amyloid plaques and neurofibrillar tangles in the cerebral cortex of such patients. Similar alterations are observed in patients with Trisomy 21 (Down's syndrome). Biochemical and immunological studies reveal that the dominant proteinaceous component of the amyloid plaque is an approximately 4.2 kilodalton (kD) protein of about 39 to 43 amino acids. This protein is designated Aβ, β-amyloid peptide, and sometimes β/A4; referred to herein as Aβ. In addition to its deposition in amyloid plaques, Aβ is also found in the walls of meningeal and parenchymal arterioles, small arteries, capillaries, and sometimes, venules. Compelling evidence accumulated during the last decade reveals that Aβ is an internal polypeptide derived from a type 1 integral membrane protein, termed β-amyloid precursor protein (APP) (Selkoe, D. *Physiol. Rev.* 2001, 81, 741-766; Wolfe, M. *J. Med. Chem.* 2001, 44, 2039-2060). βAPP is normally produced by many cells both in vivo and in cultured cells, derived from various animals and humans. Several proteolytic fragments of APP are generated by proteinases referred to as secretases. A subset of these proteolytic fragments, designated β-amyloid peptide (Aβ), contains 39 to 43 amino acids and is generated by the combined action of β-secretase and γ-secretase. β-secretase is a membrane-bound, aspartyl protease that forms the N-terminus of the Aβ peptide. The C-terminus of the Aβ peptide is formed by γ-secretase, an apparently oligomeric complex that includes presenilin-1 and/or presenilin-2. Presenilin-1 and presenilin-2 are polytopic membrane-spanning proteins that may contain the catalytic components of γ-secretase (Seiffert, D.; Bradley, J. et al., *J. Biol. Chem.* 2000, 275, 34086-34091).

In addition to AD, excess production and/or reduced clearance of Aβ causes cerebral amyloid angiopathy (CAA) (reviewed in Thal, D., Gherbremedhin, E. et al., *J. Neuropath. Exp. Neuro.* 2002, 61, 282-293). In these patients, vascular amyloid deposits cause degeneration of vessel walls and aneurysms that may be responsible for 10-15% hemorrhagic strokes in elderly patients. As in AD, mutations in the gene encoding Aβ lead to an early onset form of CAA, referred to as cerebral hemorrhage with amyloidosis of the Dutch type, and mice expressing this mutant protein develop CAA that is similar to patients.

A logical approach to reducing Aβ levels is to interfere with the action of the secretases that are directly involved in the cleavage of APP to Aβ. The β-secretase enzyme (BACE) is responsible for cleaving APP and forms the amino-terminus of Aβ, initiating the amyloidogenic pathway. The BACE enzyme is a transmembrane aspartyl protease and was described in the literature by several independent groups [see Hussain, I. et al., *Mol. Cell. Neurosci.*, 1999, 14, 419-427; Lin, X. et al., *Proceedings of the National Academy of Sciences of the United States of America* 2000, 97: 1456-1460; Sinha, S., et al., *Nature* 1999, 402, 537-540; Vassar, R., et al., *Science* 1999, 286, 735-741; Walsh, D. M., et al., *Biochemical Transactions* 2002, 30, 552-557; Wolfe, M. *J. Med. Chem.* 2001, 44, 2039-2060; Yan, R. et al., *Nature* 1999, 402, 533-537].

Removal of BACE activity in mice by gene targeting completely abolishes Aβ production [see Luo, Y., et al., *Nature Neuroscience* 2001, 4, 231-232; Roberds, S. L., et al., *Human Molecular Genetics* 2001, 10, 1317-1324]. BACE −/− mice also show no detectable negative phenotypes, suggesting that disruption of BACE-mediated cleavage of APP does not produce additional undesired effects. This demonstrates that a drug substance capable of inhibiting β-secretase activity should lower or halt the synthesis of Aβ and should provide a safe treatment for Alzheimer's disease.

PCT Publication WO 2005049585, published Jun. 2, 2005 discloses novel macrocyclic lactams for the treatment of neurological and vascular disorders related to β-amyloid generation and/or aggregation.

PCT Publication WO 2005018545 A2, published Mar. 3, 2005 discloses macrocyclic BACE inhibitors for the treatment of Alzheimers.

Published article Ghosh, A. K. et al., *Bioorganic and Medicinal Chem. Lett.* 2005, 15, 15-20 discloses macrocyclic amide-urethane inhibitors of BACE.

PCT Publication WO 2004062625 A2, published Jul. 29, 2004 discloses macrocyclic BACE inhibitors for the treatment of Alzheimers.

PCT Publication WO 2002100856 A1, published Dec. 19, 2002 discloses macrocycles useful in the treatment of Alzheimers.

Published article Stachel, S. J., et al., *J. Med. Chem.* 2006, 49, 6147-6150 discloses macrocyclic inhibitors of BACE for the treatment of Alzheimers.

Published article Cole, D. C., et al., *J. Med. Chem.* 2006, 49, 6158-6161 discloses acylguanidines inhibitors of BACE 1 for the treatment of Alzheimers.

At present there remains an urgent need to develop pharmaceutical agents capable for effective treatment in halting, slowing, preventing, and/or reversing the progression of Alzheimer's disease. Compounds that are effective inhibitors of beta-secretase, that inhibit beta-secretase mediated cleavage of APP, that are effective inhibitors of Aβ protein production by beta-secretase, and/or are effective in reducing soluble Aβ protein, amyloid beta deposits or amyloid beta plaques, are needed for effective treatment in halting, slowing, preventing, and/or reversing neurological disorders related to Aβ protein production, such as Alzheimer's disease.

SUMMARY OF THE DISCLOSURE

A series of oxime-containing macrocyclic acyl guanidines having the Formula (I)

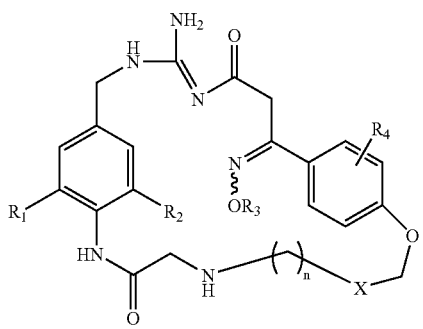

I or a stereoisomer; or a pharmaceutically acceptable salt thereof, wherein $R_1$, $R_2$, $R_3$, $R_4$, n and X as defined below are effective inhibitors of the production of β-amyloid peptide (β-AP) from β-amyloid precursor protein (β-APP). The pharmacologic action of these compounds makes them useful for treating conditions responsive to the inhibition of β-AP in a patient; e.g., Alzheimer's Disease (AD) and Down's Syndrome. Therapy utilizing administration of these compounds or a pharmaceutical composition containing a therapeutically effective amount of at least one of these compounds to patients suffering from, or susceptible to, these conditions involves reducing β-AP available for accumulation and deposition in brains of these patients.

DETAILED DESCRIPTION

The present application comprises compounds of Formula I, their pharmaceutical formulations, and their use in inhibiting β-AP production in patients suffering from or susceptible to AD or other disorders resulting from β-AP accumulation in brain tissue. The compounds of Formula I which include stereoisomers and pharmaceutically acceptable salts thereof have the following formula and meanings:

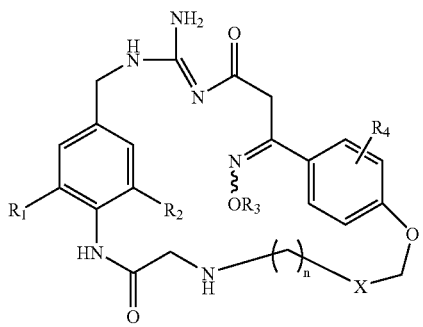

I wherein $R_1$ and $R_2$ are independently selected from hydrogen, $C_{1-4}$alkyl, halogen and $CF_3$;

$R_3$ is $C_{1-4}$alkyl, allyl, $C_{3-6}$cycloalkyl or $CF_3$;

$R_4$ is hydrogen, halogen, CN, $CF_3$, OH, —$NH_2$, $C_{1-6}$alkyl or $C_{1-6}$alkoxy;

n is an integer from 1 to 6; and

X is $(CH_2)_2$ or CH=CH.

The present application also provides a method for the treatment or alleviation of disorders associated with β-amyloid peptide, especially Alzheimer's Disease, cerebral amyloid angiopathy and Down's Syndrome, which comprises administering together with a conventional adjuvant, carrier or diluent a therapeutically effective amount of a compound of Formula (I) or a pharmaceutically acceptable salt thereof.

As used herein, the term "Aβ" denotes the protein designated Aβ, β-amyloid peptide, and sometimes β/A4, in the art. Aβ is an approximately 4.2 kilodalton (kD) protein of about 39 to 43 amino acids found in amyloid plaques, the walls of meningeal and parenchymal arterioles, small arteries, capillaries, and sometimes, venules. The isolation and sequence data for the first 28 amino acids are described in U.S. Pat. No. 4,666,829. The 43 amino acid sequence is well known in the art, see Dingwall, C. *Journal of Clinical Investigation* 2001, 108, 1243-1246; as well as PCT international patent application WO 01/92235, published Dec. 6, 2001, herein incorporated by reference in its entirety.

The term "APP", as used herein, refers to the protein known in the art as β amyloid precursor protein. This protein is the precursor for Aβ and through the activity of "secretase" enzymes, as used herein, it is processed into Aβ. Differing secretase enzymes, known in the art, have been designated β secretase, generating the N-terminus of Aβ, α secretase cleaving around the 16/17 peptide bond in Aβ, and "γ secretases", as used herein, generating C-terminal Aβ fragments ending at position 38, 39, 40, 42, and 43 or generating C-terminal extended precursors which are subsequently truncated to the above polypeptides.

As used herein and in the claims, "alkyl" or "alkylene" is intended to include both branched and straight-chain saturated aliphatic hydrocarbon groups having the specified number of carbon atoms; for example, "$C_{1-4}$ alkyl" and "$C_{1-6}$ alkyl" denotes alkyl having 1 to 4 or 1 to 6 carbon atoms. Examples of alkyl include, but are not limited to, methyl, ethyl, n-propyl, i-propyl, n-butyl, i-butyl, sec-butyl, t-butyl, pentyl and hexyl. Preferred "alkyl" group, unless otherwise specified, is "$C_{1-4}$ alkyl". Additionally, unless otherwise specified, "propyl" denotes n-propyl or i-propyl; "butyl" denotes n-butyl, i-butyl, sec-butyl, or t-butyl.

As used herein and in the claims, "alkenyl" or "alkenylene" is intended to include hydrocarbon chains of either a straight or branched configuration and one or more unsaturated carbon-carbon bonds which may occur in any stable point along the chain, for example, "$C_{2-6}$ alkenyl" include but are not limited to ethenyl, 1-propenyl, 2-propenyl, 1-butenyl, 2-butenyl, 3-butenyl, 3-methyl-2-butenyl, 2-pentenyl, 3-pentenyl, hexenyl, and the like.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

As used herein and in the claims, "halogen" refers to fluoro, chloro, bromo, and iodo. Unless otherwise specified, preferred halogens are fluoro, bromo and chloro. "Counterion" is used to represent a small, negatively charged species such as chloride, bromide, hydroxide, acetate, sulfate, and the like.

"Cycloalkyl" is intended to include saturated ring groups, having the specified number of carbon atoms. For example, "$C_{3-6}$ cycloalkyl" denotes such as cyclopropyl, cyclobutyl, cyclopentyl and cyclohexyl.

The compounds described herein may have asymmetric centers and geometric isomers of olefins and the like can also be present in the compounds described herein, and all such stable isomers are contemplated in the present invention. Cis and trans geometric isomers of the compounds of the present invention are described and may be isolated as a mixture of isomers or as separated isomeric forms. An embodiment of the geometric isomers is illustrated by the compound of formula Ia.

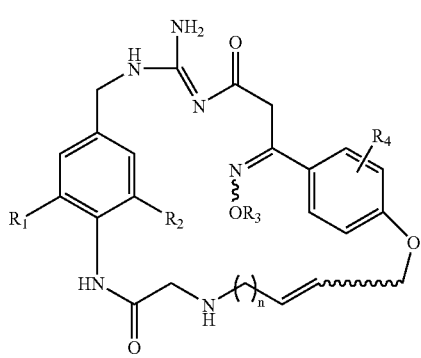

Ia

The macrocyclic acyl guanidines disclosed herein have an oxime-containing group which may exist as a syn-isomer, anti-isomer or mixtures thereof. All isomers of the oxime group are intended to be included.

Compounds of the present disclosure containing an asymmetrically substituted atom may be isolated in optically active or racemic forms. It is well known in the art how to prepare optically active forms, such as by resolution of racemic forms or by synthesis from optically active starting materials. Mixtures of isomers of the compounds of the examples or chiral precursors thereof can be separated into individual isomers according to methods which are known per se, e.g. fractional crystallization, adsorption chromatography or other suitable separation processes. Resulting racemates can be separated into antipodes in the usual manner after introduction of suitable salt-forming groupings, e.g. by forming a mixture of diastereoisomeric salts with optically active salt-forming agents, separating the mixture into diastereomeric salts and converting the separated salts into the free compounds. The enantiomeric forms may also be separated by fractionation through chiral high pressure liquid chromatography columns.

All chiral, diastereomeric, racemic forms and all geometric isomeric forms of a structure are intended, unless the specific stereochemistry or isomeric form is specifically indicated.

The phrase "nontoxic pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein and in the claims, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

In the method of the present application, the term "therapeutically effective amount" means the total amount of each active component of the method that is sufficient to show a meaningful patient benefit, i.e., healing of acute conditions characterized by inhibition of β-amyloid peptide production. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases associated with β-amyloid peptide.

The compounds of the present application can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Scheme 1 describes a general synthesis of compounds of Formula I, wherein X is CH=CH. Beta-ketoesters of formula 1, can be converted to oximes of formula 2 through treatment with a compound of formula $R_3ONH_2$.HCl salt in a polar solvent such as ethanol at 80° C. O-Alkylation of the compound of formula 2 can be carried out using allyl bromide in the presence of a base such as potassium carbonate in a polar solvent such as DMF or acetonitrile to give the compound of formula 3. The esters of formula 3 can be hydrolyzed under basic conditions such as aqueous lithium hydroxide in THF at room temperature to provide acids of formula 4. The coupling reaction of acids of formula 4 with tert-butyl amino(methylthio)methylenecarbamate (formula 5) can be effected using a coupling reagent in the presence of a base to give the compounds of formula 6. The preferred coupling reagent is benzotriazol-1-yloxytripyrrolidinophosphonium hexafluorophosphate (Py.BOP), and the preferred base is triethylamine or diisopropylethylamine. Compounds of formula 6 can be converted to the compounds of formula 8 upon treatment with amines of formula 7 in a solvent such as THF or dichloromethane. Treatment of compounds of formula 8 with 2-bromoacetyl bromide and triethylamine provides bromides of formula 9, which reacts with primary amine of formula 10 to furnish compounds of formula 11. Mono-Boc protection of the compounds of formula 11 can be performed with Boc$_2$O in the presence of a base such as triethylamine or diisopropylethylamine to give Bis-Boc derivatives of formula 12. Compounds of formula 12 can undergo ring-closing metathesis (RCM) using Grubbs catalysts (Grubbs and Chang, Tetrahedron, 1998, 4413-4450) to afford macrocycles of formula 13. Treatment of macrocycles of formula 13 with a acid such as trifluoroacetic acid (TFA) can remove both BOC protecting groups and provide compounds of formula Ia.

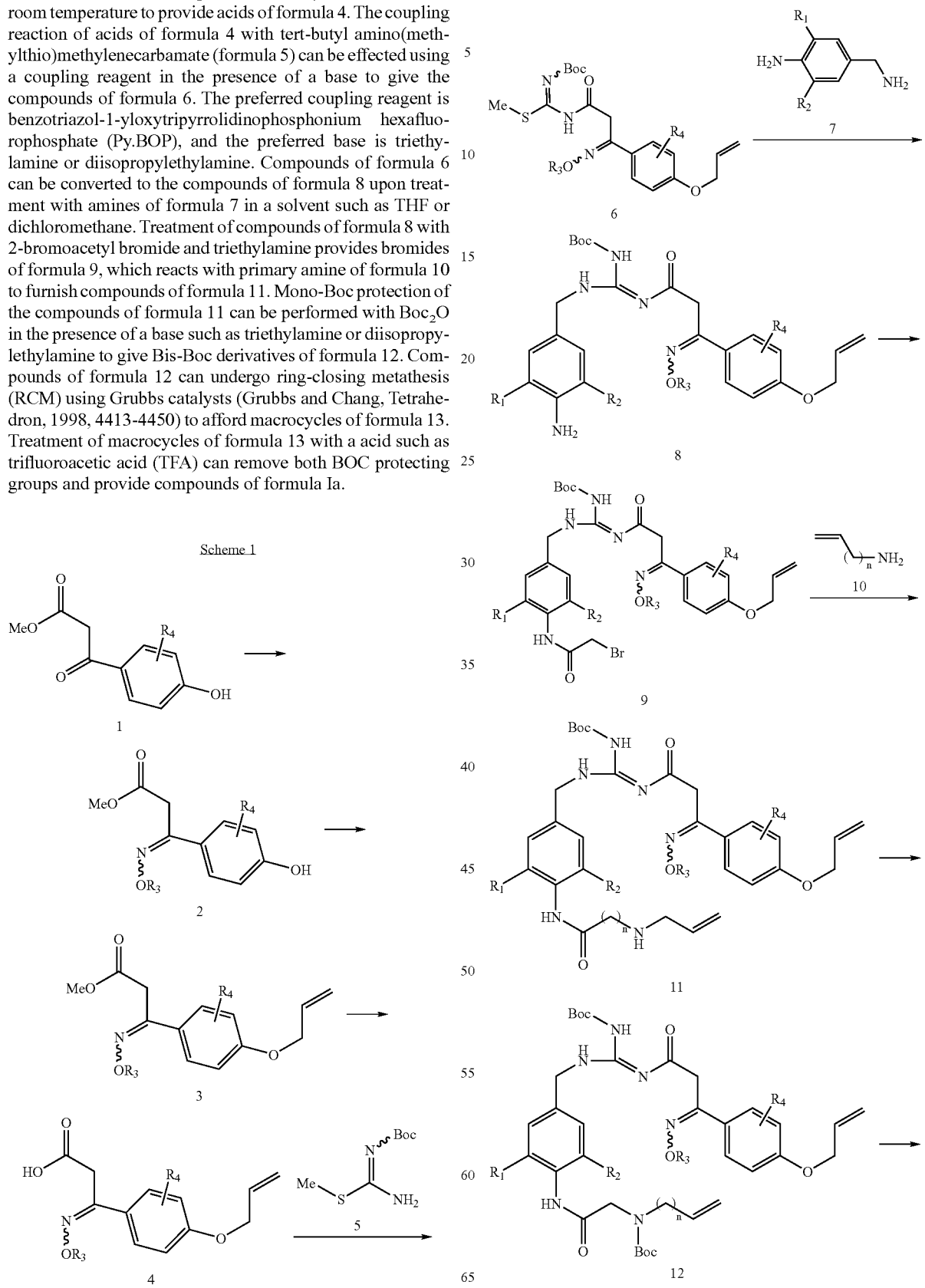

Scheme 1

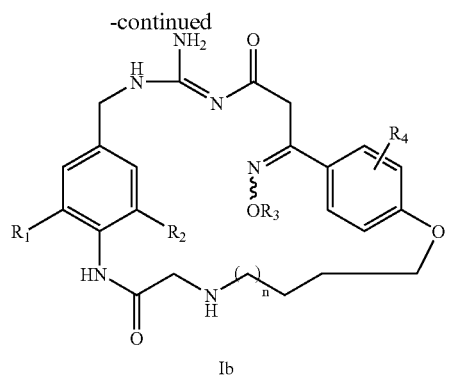

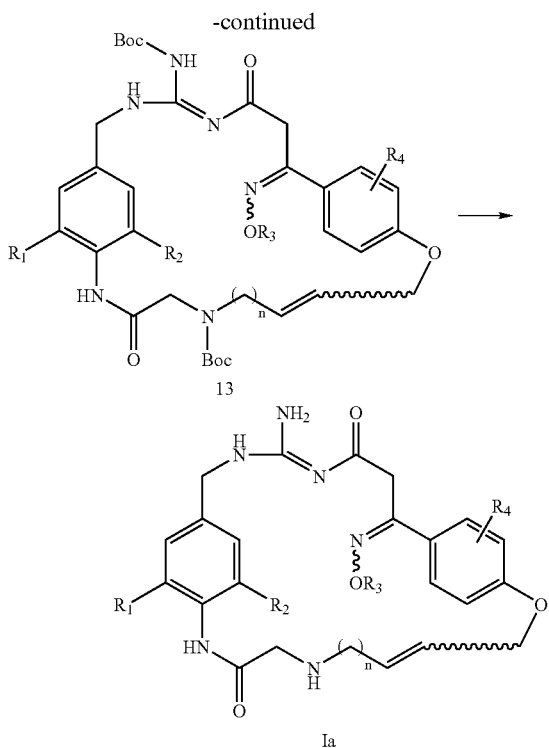

Scheme 2 describes the synthesis of compounds of formula I, wherein X is (CH$_2$)$_2$. Macrocycles of formula 13 can be hydrogenated using palladium on charcoal to give saturated macrocycles of formula 14. Treatment of macrocycles of formula 14 with a acid such as trifluoroacetic acid (TFA) can remove the BOC protecting group and provide compounds of formula Ib.

Scheme 2

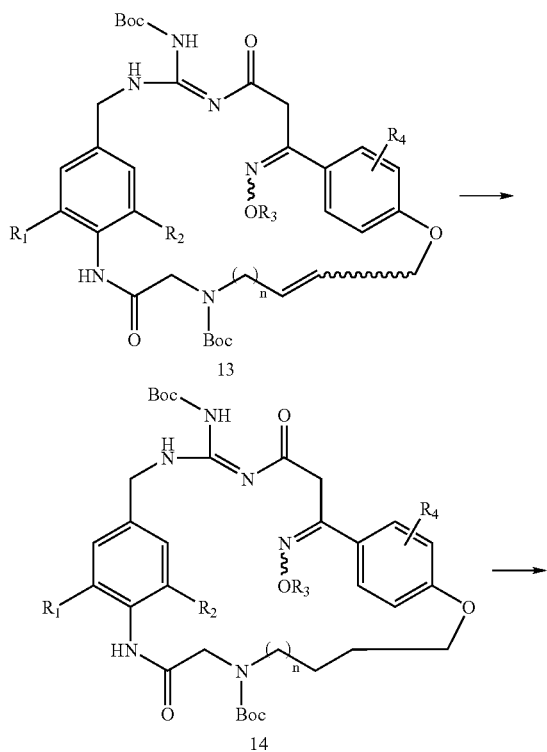

DESCRIPTION OF THE SPECIFIC EMBODIMENTS

The compounds of this application and their preparation can be understood further by the following working examples. These examples are meant to be illustrative of the present application, and are not to be taken as limiting thereof.

Chemical abbreviations used in the specification and Examples are defined as follows:

"Ac" for acetate,
"Boc" or "BOC" for t-butyloxycarbonyl,
"BOP" for benzotriazol-1-yloxytris-(dimethylamino)-phosphonium hexafluorophosphate,
"Cbz" for benzyloxycarbonyl,
"CDCl$_3$," for deuterochloroform,
"DCM" for dichloromethane
"DIEA", "Hunig's base", or "DIPEA" for N,N-diisopropylethylamine,
"DME" for 1,2-dimethoxyethane,
"DMF" for N,N-dimethylformamide,
"DMAP" for 4-dimethylaminopyridine,
"DMSO" for dimethylsulfoxide,
"EDC" or "EDCI" for 1-(3-dimethylaminopropyl)-3-ethylcarbodiimide hydrochloride,
"Et" for ethyl,
"EtOAc" for ethyl acetate,
"HoAc" for acetic acid,
"HOBt" for 1-hydroxybenzotriazole hydrate,
"HATU" for O-(7-azabenzotriazol-1-yl)-N,N,N',N'-tetramethyluronium hexafluorophosphate,
"LDA" for lithium diisopropylamide,
"LiHMDOS" for lithium bis(trimethylsilyl)amide,
"n-BuLi" for n-butyllithium,
"NMM" for 4-methylmorpholine,
"PyBOP" for benzotriazole-1-yl-oxy-tris-pyrrolidino-phosphonium hexafluorophosphate,
"TBTU" for O-(1H-benzotriazol-1-yl)-N,N,N',N'-tetramethyluronium tetrafluoroborate,
"TEA" for triethylamine,
"TES" for triethylsilane,
"TFA" for trifluoroacetic acid, and
"THF" for tetrahydrofuran.

Abbreviations used in the Examples are defined as follows: "° C." for degrees Celsius, "MS" for mass spectrometry, "ESI" for electrospray ionization mass spectroscopy, "HR" for high resolution, "LC-MS" for liquid chromatography mass spectrometry, "eq" for equivalent or equivalents, "g" for gram or grams, "h" for hour or hours, "mg" for milligram or milligrams, "mL" for milliliter or milliliters, "mmol" for millimolar, "M" for molar, "min" for minute or minutes, "rt" for room temperature, "NMR" for nuclear magnetic resonance spectroscopy, "tlc" for thin layer chromatography, "atm" for atmosphere, and "α", "β", "R", "S", "E", and "Z" are stereochemical designations familiar to one skilled in the art.

"HPLC" is an abbreviation used herein for high pressure liquid chromatography. "LC-MS" refers to high pressure liquid chromatography carried out according to the definition for HPLC with a mass spectrometry detector. HPLC solvent conditions: When described as performed under "standard conditions", samples were dissolved in methanol (1 mg/mL) and run using a gradient program with a solvent flow rate of 1.0 mL/min. The analytical reverse phase HPLC method A is as follows unless otherwise noted: Column Phenomenex Luna C18 S10 (4.6×50 mm), Start % B=0, Final % B=100, Gradient Time=2 min, Flow rate 5 ml/min, Wavelength=220 nm, Solvent A=10% MeOH—90% $H_2O$—0.1% TFA, Solvent B=90% MeOH—10% $H_2O$—0.1% TFA; and $R_t$ in min. Preparative reverse phase HPLC was performed on a Shimadzu LC-8A automated preparative HPLC system with detector (SPPD-10AV UV-VIS) wavelength and solvent systems (A and B) the same as above except where otherwise noted.

Reverse phase preparatory HPLC: When described as performed under "standard conditions", samples (approx. 20 mg) were dissolved in methanol (10 mg/mL) and purified on a 30 mm×100 mm Waters-Atlantis S5 column or a Phenomenex-Lune 30×100 mm 10 μm C18 column using a 10 minute gradient elution from 0% to 100% buffer B in buffer A (buffer A=10% MeOH/90% water/0.1% TFA and buffer B=90% MeOH/10% water/0.1% TFA) at 40 mL/minute.

Proton NMR spectra (referenced to tetramethylsilane) were obtained on a Bruker Avance 300, Avance 400, or Avance 500 spectrometer. Data were referred to the lock solvent. Electrospray Ionization (ESI) experiments were performed on a Micromass II Platform single-quadrupole mass spectrometer, or on a Finnigan SSQ7000 mass spectrometer.

The examples provided are intended to assist in a further understanding of the present disclosure. Particular materials employed, species and conditions are intended to farther illustrate the specific embodiments of the invention and not limit the reasonable scope thereof.

SYNTHESIS OF INTERMEDIATE (E)-tert-butyl (4-amino-3,5-dichlorobenzylamino)(amino)methylene carbamate

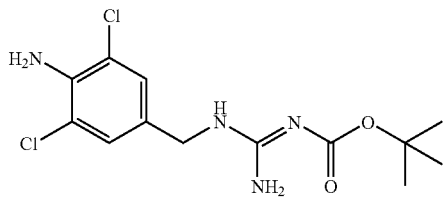

A mixture of 4-(aminomethyl)-2,6-dichlorobenzenamine (150 mg, 0.785 mmol), tert-butyl amino(methylthio)methylenecarbamate (157 mg, 0.825 mmol) and p-toluenesulfonic acid (142 mg, 0.825 mmol) in dichloromethane (4 mL) was stirred at RT for 2 days. The reaction mixture was concentrated under vacuum and purified by filtering through QAX anion exchange cartridge with methanol to provide the title compound as an off-white solid (260 mg, quantitative yield).

$^1$H NMR (400 MHz, CD$_3$OD) δ 1.453 (9H, s), 4.249 (2H, s), 7.162 (2H, s). HPLC retention time: 2.332 min (method A). MS (ESI) (M+H)$^+$ 333.02.

EXAMPLE 1

Isomer A of 4-amino-23,26-dichloro-13-oxa-3,5,18,21-tetraazatricyclo[20.2.2.2$^{9,12}$]octacosa-1(24),4,9,11,15,22,25,27-octaene-6,8,20-trione 8-(O-ethyloxime)

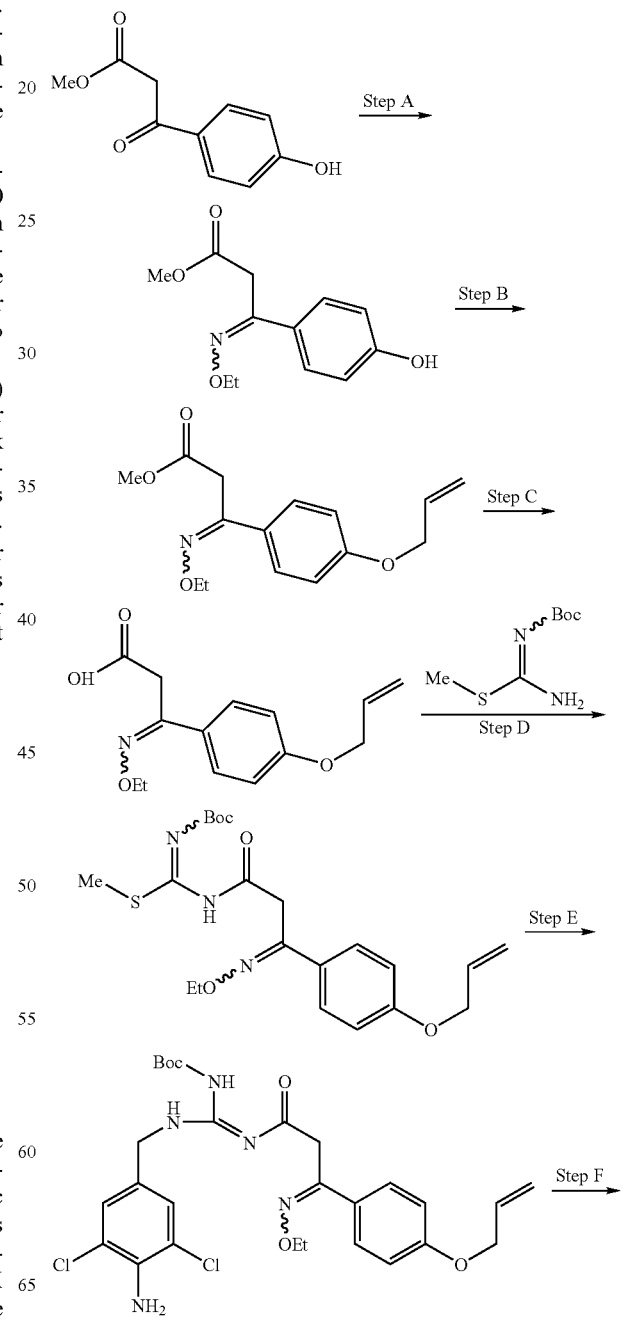

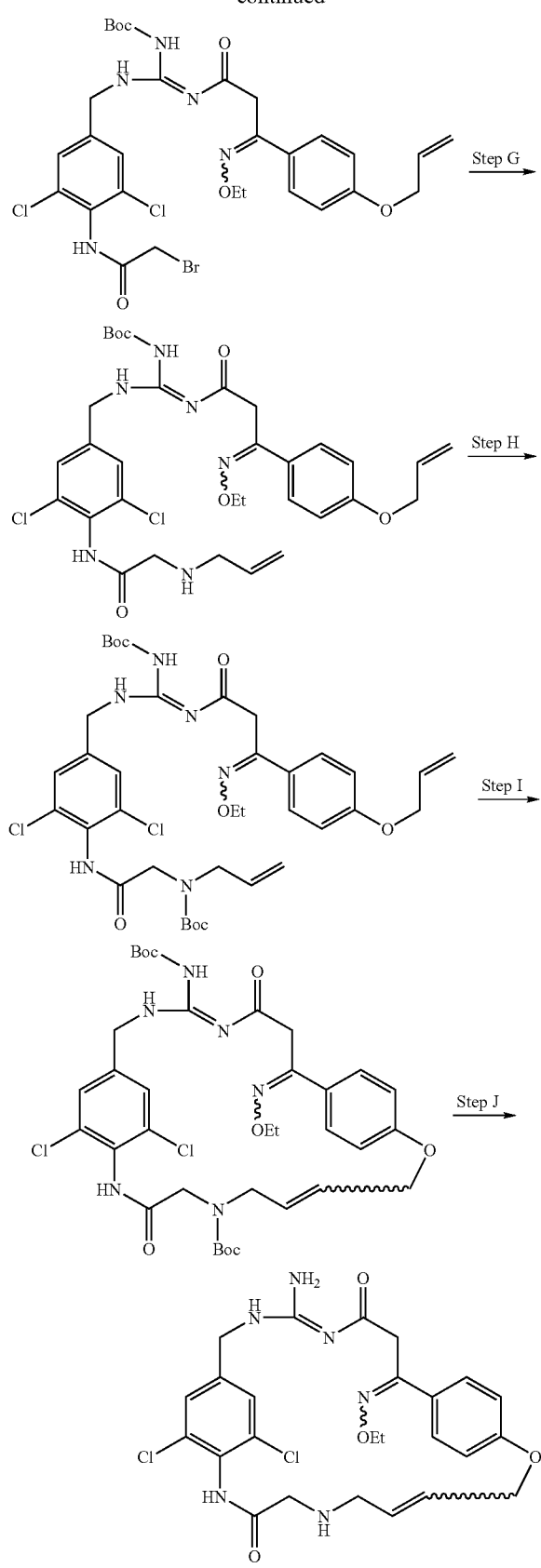

Step A: Methyl 3-(ethoxyimino)-3-(4-hydroxyphenyl)propanoate

A mixture of methyl 3-(4-hydroxyphenyl)-3-oxopropanoate (1 g) and $EtONH_2 \cdot HCl$ (600 mg) in methanol (10 mL) was heated at 65° C. for 2 h. Methanol was removed in vacuo, and saturated sodium bicarbonate was added to the residue. The aqueous solution was extracted with ethyl acetate (×4), and the combined organic layers were washed with brine, dried over anhydrous sodium sulfate, and filtered. The filtrate was evaporated in vacuo to give the title compound as a colorless oil, which was used directly in Step B. HPLC retention time: 1.51 min (method A). MS (ESI) $(M+H)^+$ 238.09.

Step B: Methyl 3-(4-(allyloxy)phenyl)-3-(ethoxyimino)propanoate

To a solution of crude methyl 3-(ethoxyimino)-3-(4-hydroxyphenyl)propanoate obtained from Step A at 0° C. was added allyl bromide (0.65 mL) and potassium carbonate (781 mg) in DMF (5 mL), and the resulting suspension was stirred at 0° C. for 2 h. Ethyl acetate and water were added, the aqueous layer was extracted with ethyl acetate (×3), and the combined organic layers were washed with brine, dried over anhydrous sodium sulfate, filtered, and evaporated in vacuo to give the title compound as an oil. The crude product was used in Step C without purification. HPLC retention time: 1.88 min (method A). MS (ESI) $(M+H)^+$ 278.14.

Step C: 3-(4-(Allyloxy)phenyl)-3-(ethoxyimino)propanoic acid

To a solution of crude methyl 3-(4-(allyloxy)phenyl)-3-(ethoxyimino)propanoate obtained from Step B in THF (7 mL) was added 1 N lithium hydroxide (10.2 mL), and the resulting solution was stirred at room temperature for 12 h. Most of the solvents were removed in vacuo, and 1N hydrochloric acid (10.2 mL) was added. The aqueous layer was extracted with ethyl acetate (×4), and the combined organic layers were washed with brine, dried over anhydrous sodium sulfate, and filtered. The filtrate was evaporated in vacuo to give the title compound as a white solid (850 mg). $^1H$ NMR (400 MHz, $CDCl_3$) δ 7.58 (2H, d, J=7.6 Hz), 6.89 (2H, d, J=7.6 Hz), 6.02 (1H, m), 5.42 (1H, m), 5.29 (1H, m), 4.54 (1H, m), 4.26 (2H, q, J=5.6 Hz), 3.78 (2H, s), 1.30 (3H, t, J=5.6 Hz).

Step D: tert-Butyl 7-(4-(allyloxy)phenyl)-5-oxo-9-oxa-2-thia-4,8-diazaundec-7-en-3-ylidenecarbamate A mixture of 3-(4-(Allyloxy)phenyl)-3-(ethoxyimino)propanoic acid from Step C (850 mg), tert-butyl amino(methylthio)methylenecarbamate (675 mg), Py.Bop (2.01 g), and triethylamine (0.68 mL) in dichloromethane (1.8 mL) was stirred at room temperature for 12 h. The crude reaction mixture was purified directly by Boitage flash chromatography eluting with 15-30% ethyl acetate/85-70% hexanes to give the title compound as a white solid (1.14 g). HPLC retention time: 2.37 min (method A). MS (ESI) $(M+Na)^+$ 436.25.

Step E: tert-Butyl-(1-(3-(4-(allyloxy)phenyl)-3-(ethoxyimino)propanoylimino)-2-(4-amino-3,5-dichlorophenyl)ethylcarbamate A solution of tert-butyl 7-(4-(allyloxy)phenyl)-5-oxo-9-oxa-2-thia-4,8-diazaundec-7-en-3-ylidenecarbamate from Step D (1.14 g) in THF (4 mL) was added 4-(aminomethyl)-2,6-dichloroaniline (647 mg) and diisopropylethylamine (0.46 mL), and the resulting mixture was heated at 58° C. for 12 h. The solvents were removed in vacuo, and the residue was purified by Biotage eluting with 10-25% ethyl acetate/90-75% hexanes to give the title compound as a yellowish oil (1.28 g). retention time: 2.37 min (method A). MS (ESI) (M+H)$^+$ 578.23.

Step F: tert-Butyl-1-(3-(4-(allyloxy)phenyl)-3-(ethoxyimino)-propanoylimino)-2-(4-(2-bromoacetamido)-3,5-dichlorophenyl)ethylcarbamate To a solution of tert-butyl-(1-(3-(4-(allyloxy)phenyl)-3-(ethoxyimino)-propanoylimino)-2-(4-amino-3,5-dichlorophenyl)ethylcarbamate from Step B (1.28 g) in dichloromethane (8 mL) at 0° C. was added triethylamine (0.34 mL) followed by 2-bromoacetyl bromide (0.21 mL), and the resulting solution was stirred at 0° C. for 1 h. 0.21 mL of 2-bromoacetyl bromide was added, and the reaction continued at 0° C. for 1 h. Saturated sodium bicarbonate was added, the aqueous solution was extracted with dichloromethane (×3), and the combined organic layers were dried over anhydrous sodium sulfate, and filtered. The filtrate was evaporated in vacuo. The crude residue was purified by preparative TLC eluting with 50% ethyl acetate/50% hexane to give the title compound as a white solid (860 mg). retention time: 2.27 min (method A). MS (ESI) (M+H)$^+$ 700.19.

Step G: tert-Butyl-2-(4-(2-(allylamino)acetamido)-3,5-dichlorophenyl)-1-(3-(4-(allyloxy)phenyl)-3-(ethoxyimino)propanoylimino)ethylcarbamate To a solution of tert-butyl-1-(3-(4-(allyloxy)phenyl)-3-(ethoxyimino)-propanoylimino)-2-(4-(2-bromoacetamido)-3,5-dichlorophenyl)ethylcarbamate (100 mg) in dichloromethane (0.30 mL) at room temperature was added allylamine (32 µL), and the resulting solution was stirred at room temperature for 2 h. The solvents were removed in vacuo to give the title compound as a white solid, which was used in Step H without purification. retention time: 2.07 min (method A). MS (ESI) (M+H)$^+$ 675.20.

Step H: tert-Butyl-2-(4-(2-(N-Boc-allylamino)acetamido)-3,5-dichlorophenyl)-1-(3-(4-(allyloxy)phenyl)-3-(ethoxyimino)propanoylimino)ethylcarbamate To a solution of crude tert-butyl-2-(4-(2-(allylamino)acetamido)-355-dichlorophenyl)-1-(3-(4-(allyloxy)phenyl)-3-(ethoxyimino)propanoylimino)ethyl-carbamate obtained from Step G in dichloromethane (0.3 mL) at room temperature was added diisopropylethylamine (73 µL) and Boc$_2$O (61 mg), and the resulting solution was stirred at room temperature for 5 h. The solvents were evaporated in vacuo, and the residue was purified by preparative TLC eluting with 40% ethyl acetate/60% hexane to give the title compound as a colorless oil (89 mg). retention time: 2.47 min (method A). MS (ESI) (M+H)$^+$ 775.29.

Step I: Isomer A and B of 4-NHBoc-18-NBoc-23,26-dichloro-13-oxa-3,5,18,21-tetraazatricyclo[20.2.2.2$^{9,12}$]octacosa-1(24),4,9,11,15,22,25,27-octaene-6,8,20-trione 8-(O-ethyloxime)

To a solution of tert-butyl-2-(4-(2-(N-Boc-allylamino)acetamido)-3,5-dichlorophenyl)-1-(3-(4-(allyloxy)phenyl)-3-(ethoxyimino)propanoylimino)ethyl-carbamate (84 mg) in dichloromethane (38 mL) at room temperature was added 1$^{st}$ generation Grubbs catalyst (19 mg), and the resulting reaction mixture was heated at 65° C. for 4 h. The solvents were evaporated in vacuo, and the residue was purified by preparative TLC eluting with 40% ethyl acetate/60% hexane to give isomer A of the title compound as a colorless oil (5 mg) and isomer B of the title compound as a colorless oil (62 mg).

Data for Isomer A:

retention time: 2.42 min (method A). MS (ES)1 (M+H)$^+$ 747.25.

$^1$H NMR (400 MHz, CDCl$_3$) δ 8.80 (br. S), 7.24 (d, J=8.8 Hz), 6.91 (br. S), 6.62 (d, J=8.8 Hz), 5.7-6.2 (m), 4/61 (d, J=6.8 Hz), 4.40 (br. S), 4.20 (q, J=7.2 Hz), 4.10 (q, J=7.2 Hz), 3.70 (br. S), 1.51 (s), 1.49 (s), 1.30 (t, J=7.2 Hz), and 1.25 (t, J=7.2 Hz).

Data for Isomer B:

retention time: 2.37 min (method A). MS (ESI) (M+H)$^+$ 747.25.

$^1$H NMR (400 MHz, CDCl$_3$) δ 8.85 (br. S), 8.20 (br. S), 7.23 (m), 6.90 (m), 6.50 (m), 5.8-6.2 (in), 4.47 (br. S), 4.42 (apparent d), 4.20 (q, J=7.2 Hz), 4.10 (q, J=7.2 Hz), 4.05 (m), 3.74 (br. S), 1.47 (s), 1.46 (s), 1.28 (t, J=7.2 Hz), 1.23 (t, J=7.2 Hz).

Step J: Isomer A of 4-amino-23,26-dichloro-13-oxa-3,5,18,21-tetraazatricyclo[20.2.2.2$^{9,12}$]octacosa-1(24),4,9,11,15,22,25,27-octaene-6,8,20-trione 8-(O-ethyloxime)

To a solution of isomer A of macrolide (5 mg) from Step I in dichloromethane (0.10 mL) at room temperature was added TFA (50 µL), and the resulting reaction mixture was stirred at room temperature for 12 h. The reaction mixture was evaporated in vacuo to give the title compound as a colorless oil (3 mg). retention time: 1.39 min (method A). MS (ESI) (M+H)$^+$ 547.14.

EXAMPLE 2

Isomer B of 4-amino-23,26-dichloro-13-oxa-3,5,18,21-tetraazatricyclo-[20.2.2.2$^{9,12}$]octacosa-1(24),4,9,11,15,22,25,27-octaene-6,8,20-trione 8-(O-ethyloxime)

To a solution of isomer B of macrolide (6 mg) from Example 1, Step I, in dichloromethane (0.10 mL) at room temperature was added TFA (50 µL), and the resulting reaction mixture was stirred at room temperature for 6 h. The reaction mixture was evaporated in vacuo to give the TFA salt of isomer B of the title compound as a colorless oil (3 mg). retention time: 1.33 min (method A). MS (ESI) (M+H)$^+$ 547.14.

EXAMPLE 3

4-Amino-23,26-dichloro-13-oxa-3,5,18,21-tetraazatricyclo[20.2.2.2$^{9,12}$]-octacosa-1(24),4,9,11,22,25,27-heptaene-6,8,20-trione 8-(O-ethyloxime)

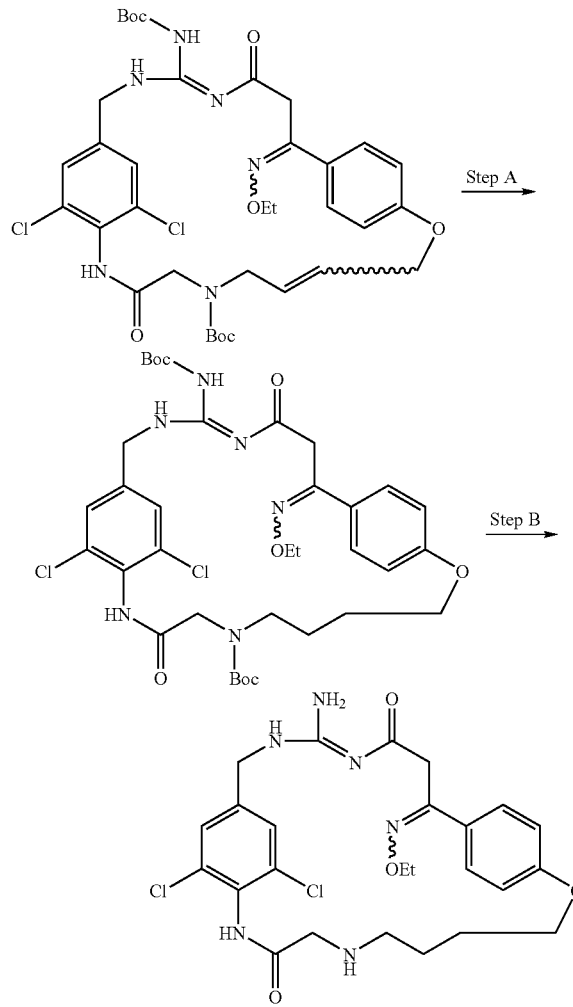

Step A: 4-NHBoc-18-NBoc-23,26-dichloro-13-oxa-3,5,18,21-tetraazatricyclo[20.2.2.2$^{9,12}$]octacosa-1(24),4,9,11,22,25,27-heptaene-6,8,20-trione 8-(O-ethyloxime)

To a solution of isomer B of macrolide from Example 1, Step 1 (5 mg) in ethyl acetate (0.60 mL) was added 10% Pd/C (one spatula-tip), and the resulting mixture was stirred under a hydrogen balloon atmosphere for 2 h. The reaction mixture was passed through a pad of Celite, and the filtrate was evaporated in vacuo to give the title compound as a colorless oil (5 mg). retention time: 2.44 min (method A). MS (ESI) (M+H)$^+$ 748.28.

Step B: 4-Amino-23,26-dichloro-13-oxa-3,5,18,21-tetraazatricyclo[20.2.2.2$^{9,12}$]-octacosa-1(24),4,9,11,22,25,27-heptaene-6,8,20-trione 8-(O-ethyloxime)

To a solution of macrocycle from Step A (6 mg) in dichloromethane (0.10 mL) at room temperature was added TFA (50 μL), and the resulting reaction mixture was stirred at room temperature for 2 h. The reaction mixture was evaporated in vacuo to give the TFA salt of the title compound as a colorless oil (6 mg). retention time: 1.37 min (method A). MS (ESI) (M+H)$^+$ 549.15.

EXAMPLE 4

Isomer A of 4-amino-24,27-dichloro-13-oxa-3,5,19,22-tetraazatricyclo-[21.2.2.29,12]nonacosa-1(25),4,9,11,15,23,26,28-octaene-6,8,21-trione 8-(O-ethyloxime)

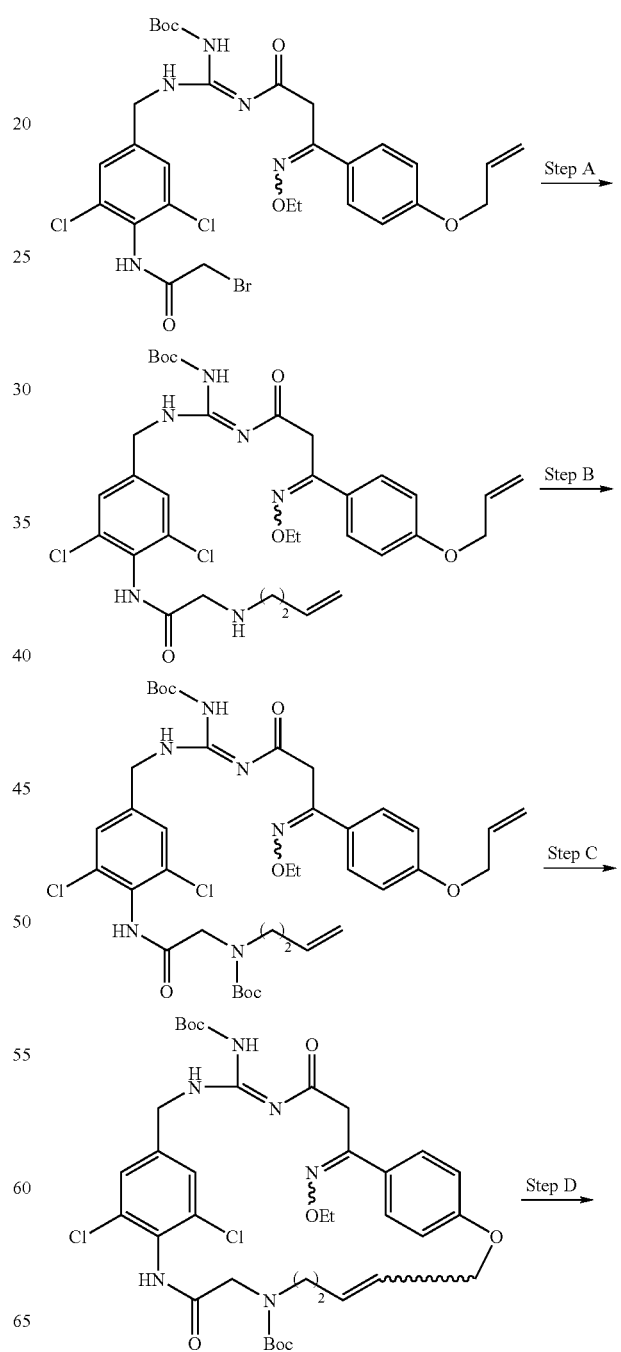

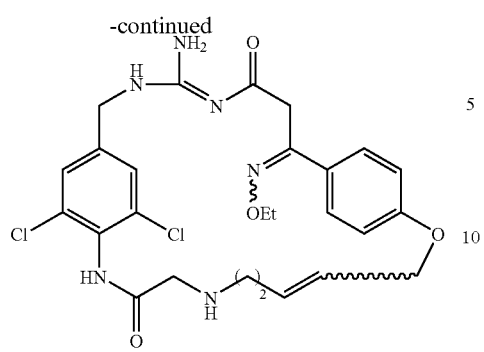

Step A: tert-Butyl-1-(3-(4-(allyloxy)phenyl)-3-(ethoxyimino)-propanoylimino)-2-(4-(2-(but-3-enylamino)acetamido)-3,5-dichlorophenyl)ethyl-carbamate To a solution of tert-butyl-1-(3-(4-(allyloxy)phenyl)-3-(ethoxyimino)-propanoylimino)-2-(4-(2-bromoacetamido)-3,5-dichlorophenyl)ethylcarbamate (100 mg) in dichloromethane (0.30 mL) at room temperature was added but-3-en-1-amine hydrochloride (45 mg) and diisopropylethylamine (97 μL), and the resulting solution was stirred at room temperature for 2 h. The solvents were removed in vacuo to give the title compound as a white solid, which was used for Step B without purification. retention time: 2.11 min (method A). MS (ESI) (M+H)+ 689.20.

Step B: tert-Butyl-2-(4-(2-(N-Boc-but-3-enylamino)acetamido)-3,5-dichlorophenyl)-1-(3-(4-(allyloxy)phenyl)-3-(ethoxyimino)propanoylimino)ethyl-carbamate To a solution of crude tert-butyl-2-(4-(2-(but-3-enylamino)acetamido)-3,5-dichlorophenyl)-1-(3-(4-(allyloxy)phenyl)-3-(ethoxyimino)propanoylimino)-ethyl-carbamate obtained from Step A in dichloromethane (0.3 mL) at room temperature was added diisopropylethylamine (73 μL) and Boc$_2$O (61 mg), and the resulting solution was stirred at room temperature for 5 h. The solvents were evaporated in vacuo, and the residue was purified by preparative TLC eluting with 40% ethyl acetate/60% hexane to give the title compound as a colorless oil (90 mg). retention time: 2.47 min (method A). MS (ESI) (M+H)+ 789.30.

Step C: Isomer A and B of 4-NHBoc-19-NBoc-24,27-dichloro-13-oxa-3,5,19,22-tetraazatricyclo[21.2.2.2$^{9,12}$]nonacosa-1(25),4,9,11,15,23,26,28-octaene-6,8,21-trione 8-(O-ethyloxime)

To a solution of tert-butyl-2-(4-(2-N-Boc-but-3-enylamino)acetamido)-3,5-dichlorophenyl)-1-(3-(4-(allyloxy)phenyl)-3-(ethoxyimino)propanoylimino)-ethyl-carbamate (90 mg) in dichloromethane (38 mL) at room temperature was added 1$^{st}$ generation Grubbs catalyst (19 mg),7 and the resulting reaction mixture was heated at 65° C. for 4 h. The solvents were evaporated in vacuo, and the residue was purified by preparative TLC eluting with 40% ethyl acetate/60% hexane to give isomer A of the title compound as a colorless oil (26 mg) and isomer B of the title compound as a colorless oil (34 mg).

Data for Isomer B:
retention time: 2.40 min (method A). MS (ESI) (M+H)+ 767.31.
$^1$H NMR (400 MHz, CDCl$_3$) δ 8.80 (br. S), 7.39 (d, J=8.4 Hz), 6.81 (br. S), 6.50 (d, J=8.8 Hz), 5.7-6.2 (m), 4.50 (d), 4.27 (d, J=4.8 Hz), 4.20 (q, J=7.2 Hz), 4.10 (q, J=7.2 Hz), 3.98 (s), 3.83 (s), 3.48 (t), 2.62 (br. S), 1.51 (s), 1.46 (s), 1.28 (t, J=7.2 Hz), and 1.25 (t, J=7.2 Hz).

Data for Isomer A:
retention time: 2.38 min (method A). MS (ESI) (M+H)+ 761.31.
$^1$H NMR (400 MHz, CDCl$_3$) δ 8.85 (hr. S), 8.50 (hr. S), 7.39 (d, J=8.8 Hz), 6.90 (m), 6.55 (m), 5.5-5.9 (m), 4.45 (br. S), 4.42 (d, J=4.8 Hz), 4.20 (q, J=7.2 Hz), 4.10 (q, J=7.2 Hz), 4.04 (s), 3.80 (br. S), 3.50 (br. S), 2.51 (br. S), 1.48 (s), 1.47 (s), 1.28 (t, J=7.2 Hz), 1.23 (t, J=7.2 Hz).

Step D: Isomer A of 4-amino-24,27-dichloro-13-oxa-3,5,19,22-tetraazatricyclo-[21.2.2.2$^{9,12}$]nonacosa-1(25),4,9,11,15,23,26,28-octaene-6,8,21-trione 8-(O-ethyloxime)

To a solution of isomer A of macrocycle 13 (R$_1$=R$_2$=Cl, R$_3$=Et, R$_4$=H, n=2) (4 mg) from Step C in dichloromethane (0.15 mL) at room temperature was added TFA (50 μL), and the resulting reaction mixture was stirred at room temperature for 12 h. The reaction mixture was evaporated in vacuo to give the TFA salt of the title compound as a colorless oil (4 mg). retention time: 1.41 min (method A). MS (ESI) (M+H)+ 561.18.

EXAMPLE 5

Isomer B of 4-amino-24,27-dichloro-13-oxa-3,5,19,22-tetraazatricyclo-[21.2.2.2$^{9,12}$]nonacosa-1(25),4,9,11,15,23,26,28-octaene-6,8,21-trione 8-(O-ethyloxime)

To a solution of isomer B of macrocycle (5 mg) from Example 4, Step C, in dichloromethane (0.10 mL) at room temperature was added TFA (50 μL), and the resulting reaction mixture was stirred at room temperature for 6 h. The reaction mixture was evaporated in vacuo to give the TFA salt of the title compound as a colorless oil (5 mg). retention time: 1.43 min (method A). MS (ESI) (M+H)+ 561.16.

EXAMPLE 6

4-Amino-24,27-dichloro-13-oxa-3,5,19,22-tetraazatricyclo[21.2.2.2$^{9,12}$]-nonacosa-1(25),4,9,11,23,26,28-heptaene-6,8,21-trione 8-(O-ethyloxime

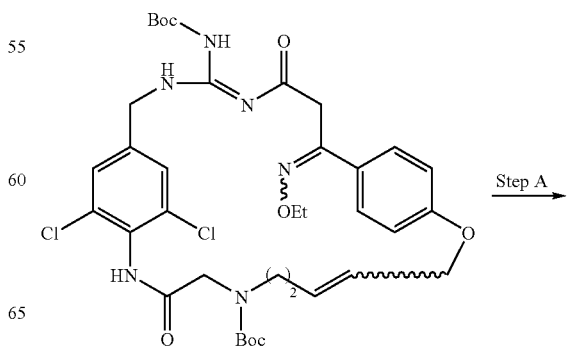

Step A

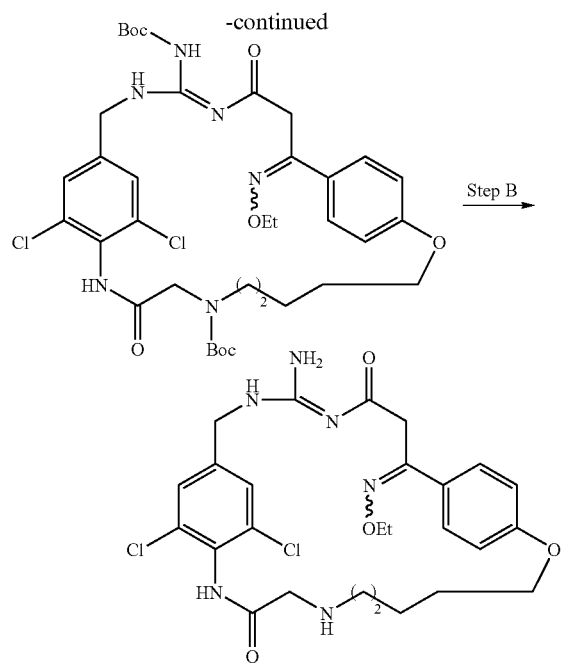

Step A: 4-NHBoc-19-NBoc-24,27-dichloro-3-oxa-3, 5,19,22-tetraazatricyclo-[21.2.2.2$^{9,12}$]nonacosa-1 (25),4,9,11,23,26,28-heptaene-6,8,2,1-trione 8-(O-ethyloxime)

To a solution of isomer A from Example 4, Step C of macrocycle (8 mg) in ethyl acetate (0.20 mL) was added 10% Pd/C (one spatula-tip), and the resulting mixture was stirred under a hydrogen balloon atmosphere for 12 h. The reaction mixture was passed through a pad of Celite, and the filtrate was evaporated in vacuo to give the title compound as a colorless oil (8 mg). retention time: 2.36 min (method A). MS (ESI) (M+f)$^+$ 763.24.

Step B: 4-Amino-24,27-dichloro-13-oxa-3,5,19,22-tetraazatricyclo[21.2.2.2$^{9,12}$]-nonacosa-1(25),4,9,11, 23,26,28-heptaene-6,8,21-trione 8-(O-ethyloxime To a solution of macrocycle from Step A (8 mg) in dichloromethane (0.10 mL) at room temperature was added TFA (50 µL), and the resulting reaction mixture was stirred at room temperature for 12 h. The reaction mixture was evaporated in vacuo to give the TFA salt of the title compound as a colorless oil (6 mg). retention time: 1.43 min (method A). MS (ESI) (M+H)$^+$ 563.15.

EXAMPLE 7

Isomer A of 4-amino-25,28-dichloro-13-oxa-3,5,20, 23-tetraazatricyclo[22.2.2.2$^{9,12}$]triaconta-1(26),4,9, 11,15,24,27,29-octaene-6,8,22-trione 8-(O-ethyloxime)

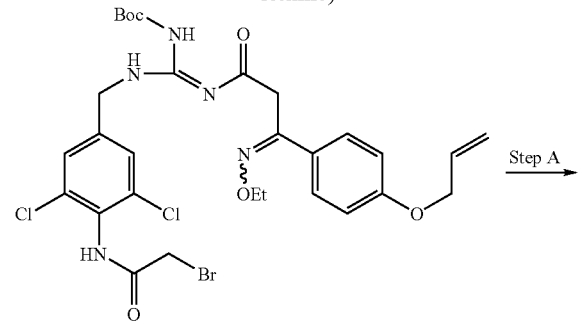

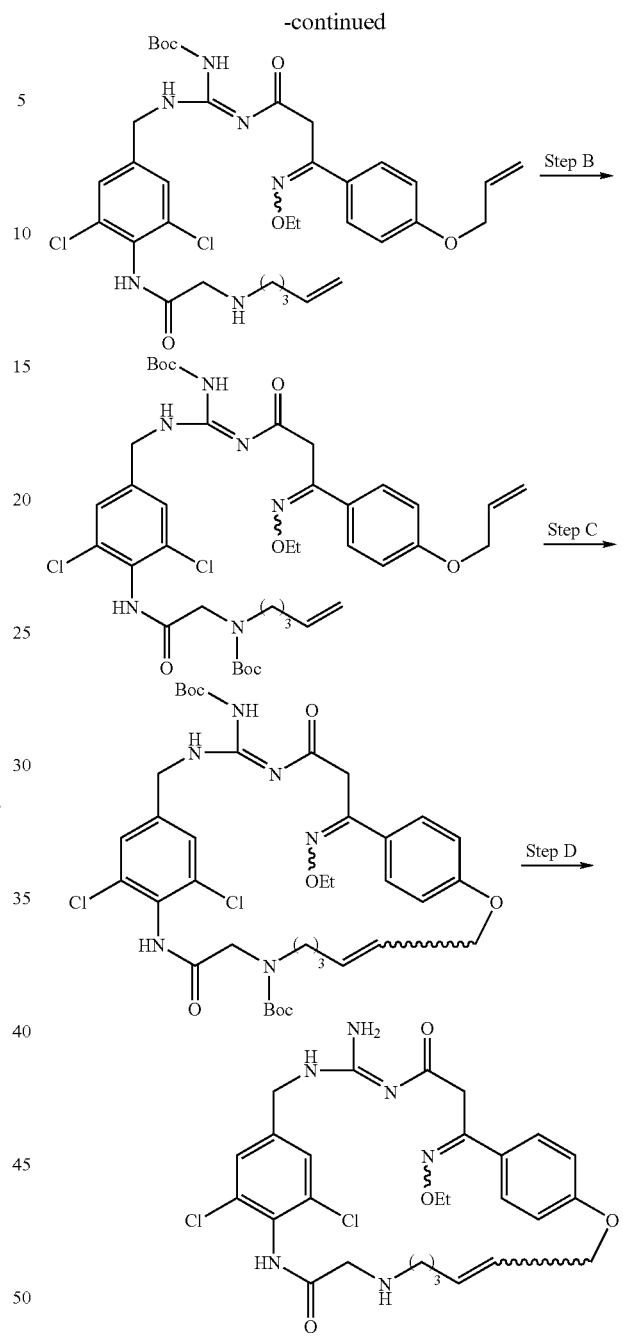

Step A: tert-Butyl-1-(3-(4-(allyloxy)phenyl)-3-(ethoxyimino)-propanoylimino)-2-(4-(2-(pent-4-enylamino)acetamido)-3,5-dichlorophenyl)ethylcarbamate To a solution of tert-butyl-1-(3-(4-(allyloxy)phenyl)-3-(ethoxyimino)-propanoylimino)-2-(4-(2-bromoacetamido)-3,5-dichlorophenyl)ethylcarbamate (100 mg) in dichloromethane (0.30 mL) at room temperature was added pent-4-en-1-amine hydrochloride (51 mg) and diisopropylethylamine (97 µL), and the resulting solution was stirred at room temperature for 2 h. The solvents were removed in vacuo to give the title compound as a white solid, which was used in Step B without purification. retention time: 2.14 min (method A). MS (ESI) (M+H)+ 703.24.

Step B: tert-Butyl-2-(4-(2-N-Boc-pent-4-enylamino) acetamido)-3,5-dichlorophenyl)-1-(3-(4-(allyloxy) phenyl)-3-(ethoxyimino)propanoylimino)ethyl-carbamate To a solution of crude tert-butyl-2-(4-(2-(ent-4-enylamino) acetamido)-3,5-dichlorophenyl)-1-(3-(4-(allyloxyphenyl)-3-(ethoxyimino)propanoylimino)-ethyl-carbamate obtained from Step A in dichloromethane (0.3 mL) at room temperature was added diisopropylethylamine (73 μL) and Boc$_2$O (61 mg), and the resulting solution was stirred at room temperature for 5 h. The solvents were evaporated in vacuo, and the residue was purified by preparative TLC eluting with 40% ethyl acetate/60% hexane to give the title compound as a colorless oil (91 mg). retention time: 2.43 min (method A). MS (ESI) (M+H)+ 803.35.

Step C: Isomer A and B of 4-NHBoc-20-NBoc-25, 28-dichloro-13-oxa-3,5,20,23-tetraazatricyclo [22.2.2.29,12]triaconta-1(26),4,9,11,15,24,27,29-octaene-6,8,22-trione 8-(O-ethyloxime)

To a solution of tert-butyl-2-(4-(2-(N-Boc-pent-4-enylamino)acetamido)-3,5-dichlorophenyl)-1-(3-(4-(allyloxy) phenyl)-3-(ethoxyimino)propanoylimino)-ethyl-carbamate (80 mg) in dichloromethane (38 mL) at room temperature was added 1$^{st}$ generation Grubbs catalyst (19 mg), and the resulting reaction mixture was heated at 65° C. for 1.5 h. The solvents were evaporated in vacuo, and the residue was purified by preparative TLC eluting with 40% ethyl acetate/60% hexane to give isomer A of the title compound as a colorless oil (54 mg) and isomer B of the title compound as a colorless oil (10 mg).

Data for Isomer B:
retention time: 2.48 min (method A). MS (ESI) (M+H)+ 775.28.
$^1$H NMR (400 MHz, CDCl$_3$) δ 8.85 (br. S), 7.43 (d, J=8.8 Hz), 7.05 (s), 6.64 (d, J=8.8 Hz), 5.63 (m), 4.45 (m), 4.38 (d, J=6.0 Hz), 4.21 (q, J=7.2 Hz), 4.10 (q, J=7.2 Hz), 4.02 (s), 3.76 (S), 3.44 (apparent t), 2.20 (m), 1.70 (m), 1.49 (s), 1.46 (s), 1.28 (t, J=7.2 Hz), 1.23 (t, J=7.2 Hz).

Data for Isomer A:
retention time: 2.44 min (method A). MS (ESI) (M+H)+ 775.29.
$^1$H NMR (400 MHz, CDCl$_3$) δ 8.80 (apparent d), 7.53 (d, J=8.8 Hz), 7.24 (br. S), 6.75 (apparent d), 5.6-5.9 (m), 4.52 (d. J=5.2 Hz), 4.46 (d, J=6.4 Hz), 4.21 (q, J=7.2 Hz), 4.10 (q, J=7.2 Hz), 4.05 (s), 3.84 (s), 3.38 (t), 2.10 (m), 1.75 (m), 1.49 (s), 1.45 (s), 1.29 (t, J=7.2 Hz), and 1.24 (t, 37.2 Hz).

Step D: Isomer A of (4E,8E,15E)-4-amino-25,28-dichloro-13-oxa-3,5,20,23-tetraazatricyclo[22.2.2. 2$^{9,12}$]triaconta-1(26),4,9,11,15,24,27,29-octaene-6,8, 22-trione 8-(O-ethyloxime)

To a solution of isomer A of macrocycle (3 mg) from Step C in dichloromethane (0.15 mL) at room temperature was added TEA (50 μL), and the resulting reaction mixture was stirred at room temperature for 12 h. The reaction mixture was evaporated in vacuo to give the TFA salt of the title compound as a colorless oil (3 mg). retention time: 1.50 min (method A). MS (ESI) (M+H)+ 575.14.

EXAMPLE 8

Isomer B of 4-amino-25,28-dichloro-13-oxa-3,5,20, 23-tetraazatricyclo-[22.2.2.29,12]triaconta-1(26),4,9, 11,15,24,27,29-octaene-6,8,22-trione 8-(O-ethyloxime)

To a solution of isomer B of macrocycle (5 mg) from Example 7, Step C, in dichloromethane (0.10 mL) at room temperature was added TFA (50 μL), and the resulting reaction mixture was stirred at room temperature for 12 h. The reaction mixture was evaporated in vacuo to give the TFA salt of the title compound as a colorless oil (5 mg). retention time: 1.52 min (method A). MS (ESI) (M+H)+ 575.16.

EXAMPLE 9

4-Amino-25,28-dichloro-13-oxa-3,5,20,23-tetraaza-tricyclo[22.2.2.2$^{9,12}$]-triaconta-1(26),4,9,11,24,27, 29-heptaene-6,8,22-trione 8-(O-ethyloxime)

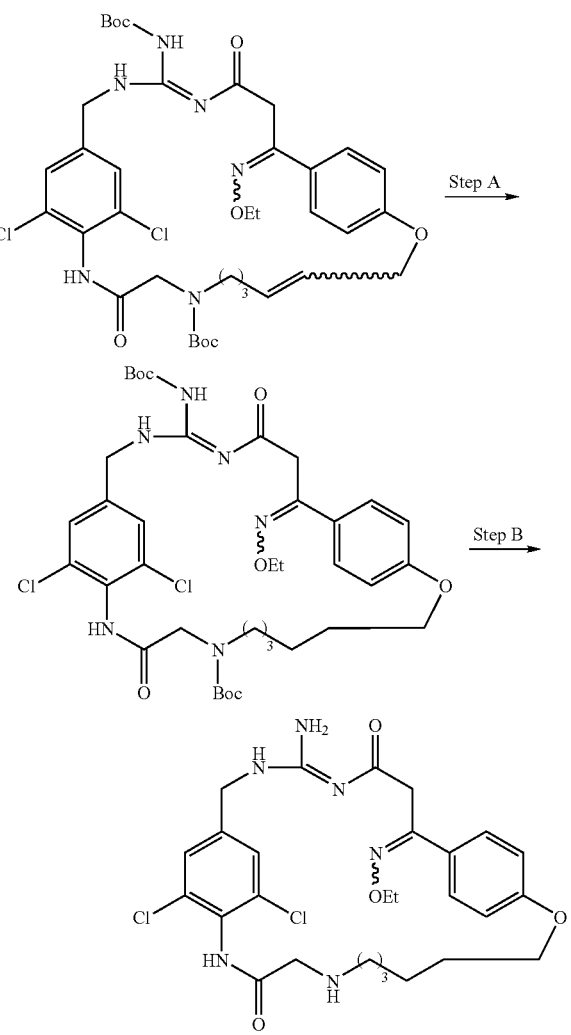

Step A: 4-NHBoc-20-NBoc-25,28-dichloro-13-oxa-3,5,20,23-tetraazatricyclo-[22.2.2.29,12]triaconta-1(26),4,9,11,24,27,29-heptaene-6,8,22-trione 8-(O-ethyloxime)

To a solution of isomer A from Example 7 (54 mg) in ethyl acetate (0.50 mL) was added 10% Pd/C (one spatula-tip), and the resulting mixture was stirred under a hydrogen balloon atmosphere for 12 h. The reaction mixture was passed through a pad of Celite, and the filtrate was evaporated in vacuo to give the title compound as a colorless oil (55 mg). retention time: 2.46 min (method A). MS (ESI) (M+H)+ 777.38. $^1$H NMR (400 MHz, CDCl$_3$) δ 8.75 (t), 7.51 (d, J=8.8 Hz), 7.03 (s), 6.70 (d, J=8.8 Hz), 4.43 (d, J=6.4 Hz), 4.21 (q, J=7.2 Hz), 4.10 (q, J=7.2 Hz), 4.01 (s), 3.90 (t), 3.78 (s), 3.40 (t), 1.70 (t), 1.60 (m), 1.49 (s), 1.45 (s), 1.29 (t, J=7.2 Hz), 1.22 (t, J=7.2 Hz).

Step B: (4-amino-25,28-dichloro-13-oxa-3,5,20,23-tetraazatricyclo-[22.2.2.29,12]triaconta-1(26),4,9,11,24,27,29-heptaene-6,8,22-trione 8-(O-ethyloxime)

To a solution of macrocycle from Step A (55 mg) in dichloromethane (0.20 mL) at room temperature was added TFA (0.10 mL), and the resulting reaction mixture was stirred at room temperature for 12 h. The reaction mixture was evaporated in vacuo to give the TFA salt of the title compound as a colorless oil (52 mg). retention time: 1.52 min (method A). MS (ESI) (M+H)+ 577.23.

EXAMPLE 10

4-Amino-26,29-dichloro-13-oxa-3,5,21,24-tetraazatricyclo-[23.2.2.2$^{9,12}$]hentriaconta-1(27),4,9,11,15,25,28,30-octaene-6,8,23-trione 8-(O-ethyloxime)

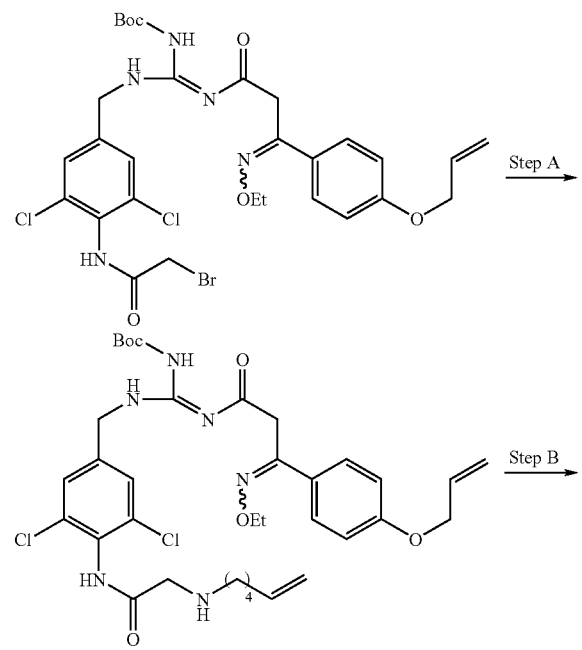

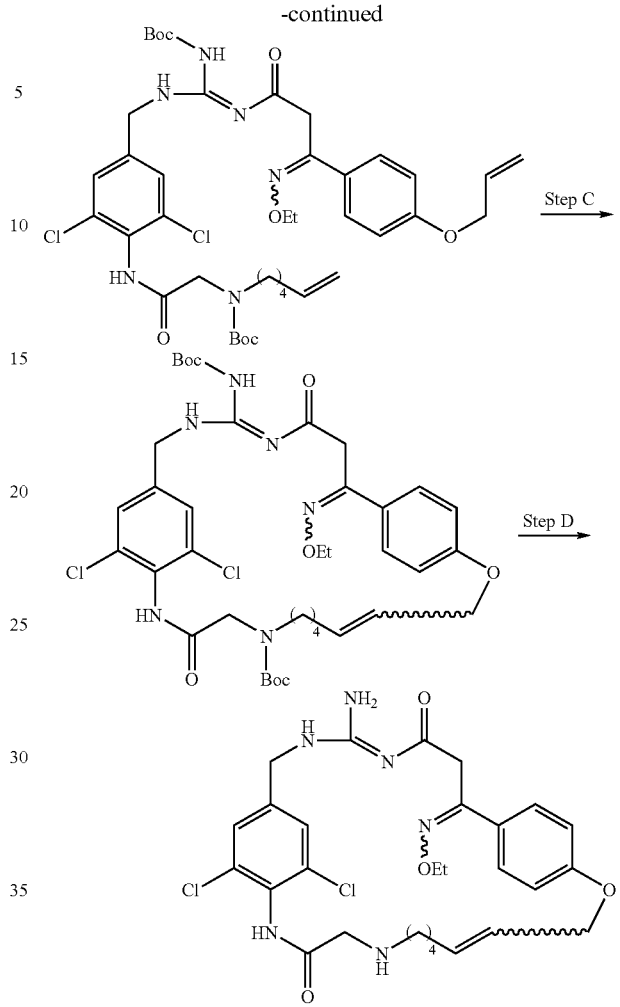

Step A: tert-Butyl-1-(3-(4-(allyloxy)phenyl)-3-(ethoxyimino)-propanoylimino)-2-(4-(2-(hex-5-enylamino)acetamido)-3,5-dichlorophenyl)ethyl-carbamate To a solution of tert-butyl-1-(3-(4-(allyloxy)phenyl)-3-(ethoxyimino)-propanoylimino)-2-(4-(2-bromoacetamido)-3,5-dichlorophenyl)ethylcarbamate (60 mg) in dichloromethane (0.30 mL) at room temperature was added pent-4-en-1-amine hydrochloride (47 mg) and diisopropylethylamine (76 µL), and the resulting solution was stirred at room temperature for 4 h. The solvents were removed in vacuo to give the title compound as a white solid, which was used in Step B without purification. retention time: 2.10 min (method A). MS (ESI) (M+H)+ 717.83.

Step B: tert-Butyl-2-(4-(2-(N-Boc-hex-5-enylamino)acetamido)-3,5-dichlorophenyl)-1-(3-(4-(allyloxy)phenyl)-3-(ethoxyimino)propanoylimino)ethyl-carbamate To a solution of crude tert-butyl-2-(4-(2-(hex-5-enylamino)acetamido)-3,5-dichlorophenyl)-1-(3-(4-(allyloxy)phenyl)-3-(ethoxyimino)propanoylimino)-ethyl-carbamate obtained from Step A in dichloromethane (0.25 mL) at room temperature was added diisopropylethylamine (45 μL) and Boc₂O (37 mg), and the resulting solution was stirred at room temperature for 2 h. The solvents were evaporated in vacuo, and the residue was purified by preparative TLC eluting with 40% ethyl acetate/60% hexane to give the title compound as a colorless oil (38 mg). retention time: 2.57 min (method A). MS (ESI) (M+H)⁺ 817.42.

Step C: 4-NHBoc-21-NBoc-26,29-dichloro-13-oxa-3,5,21,24-tetraazatricyclo[23.2.2.29,12]hentriaconta-1(27),4,9,11,15,25,28,30-octaene-6,8,23-trione 8-(O-ethyloxime)

To a solution of tert-butyl-2-(4-(2-(N-Boc-hex-5-eny-lamino)acetamido)-3,5-dichlorophenyl)-1-(3-(4-(allyloxy) phenyl)-3-(ethoxyimino)propanoylimino)-ethyl-carbamate (36 mg) in dichloromethane (15 mL) at room temperature was added 1ˢᵗ generation Grubbs catalyst (8 mg), and the resulting reaction mixture was heated at 65° C. for 2 h. The solvents were evaporated in vacuo, and the residue was purified by preparative TLC eluting with 40% ethyl acetate/60% hexane to give the title compound as a colorless oil (28 mg). retention time: 2.508 min (method A). MS (ESI) (M+H)⁺ 789.36. ¹H NMR (400 MHz, CDCl₃) δ 8.75 (m), 7.55 (d, J=4.8 Hz), 7.00 (m), 6.76 (d, J=8.8 Hz), 5.5-5.8 (m), 4.3-4-6 (m), 4.21 (, J=7.2 Hz), 4.10 (q, J=7.2 Hz), 4.01 (d, J=6.8 Hz), 3.80 (d, J=9.2 Hz), 3.35 (t, J=7.6 Hz), 2.15 (br. S), 1.65 (br. S), 1.49 (s), 1.44 (s), 1.28 (t, J=7.2 Hz), 1.24 (t, J=7.2 Hz).

Step D: 4-Amino-26,29-dichloro-13-oxa-3,5,21,24-tetraazatricyclo-[23.2.2.2⁹,¹²]hentriaconta-1(27),4,9,11,15,25,28,30-octaene-6,8,23-trione 8-(O-ethyloxime)

To a solution of macrocycle (5 mg) from Step C in dichloromethane (0.10 mL) at room temperature was added TFA (50 μL), and the resulting reaction mixture was stirred at room temperature for 2 h. The reaction mixture was evaporated in vacuo to give the TFA salt of the title compound (mixture of isomers) as a colorless oil (5 mg). retention time: 1.55 min (method A). MS (ESI) (M+H)⁺ 589.22.

EXAMPLE 11

4-Amino-26,29-dichloro-13-oxa-3,5,21,24-tetraazatricyclo-[23.2.2.2⁹,¹²]hentriaconta-1(27),4,9,11,25,28,30-heptaene-6,8,23-trione 8-(O-ethyloxime)

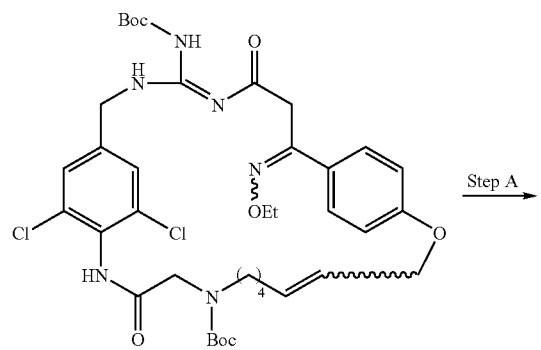

Step A

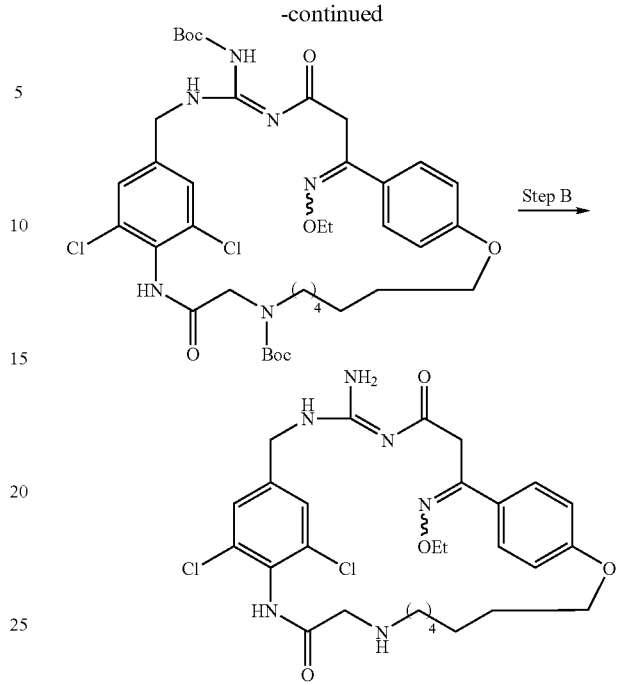

Step B

Step A: 4-NHBoc-21-NBoc-26,29-dichloro-13-oxa-3,5,21,24-tetraazatricyclo[23.2.2.29,12]hentriaconta-1(27),4,9,11,25,28,30-heptaene-6,8,23-trione 8-(O-ethyloxime)

To a solution of macrocycle from Example 10, Step C (6 mg) in ethyl acetate (0.50 mL) was added 10% Pd/C (one spatula-tip), and the resulting mixture was stirred under a hydrogen balloon atmosphere for 2 h. The reaction mixture was passed through a pad of Celite, and the filtrate was evaporated in vacuo to give the title compound as a colorless oil (5 mg). retention time: 2.49 min (method A). MS (ESI) (M+H)⁻ 791.37.

Step B: 4-Amino-26,29-dichloro-13-oxa-3,5,21,24-tetraazatricyclo-[23.2.2.29,12]hentriaconta-1(27),4,9,11,25,28,30-heptaene-6,8,23-trione 8-(O-ethyloxime)

To a solution of macrocycle from Step A (5 mg) in dichloromethane (0.10 mL) at room temperature was added TFA (50 μL), and the resulting reaction mixture was stirred at room temperature for 1 h. The reaction mixture was evaporated in vacuo to give the TFA salt of the title compound as a colorless oil (5 mg). retention time: 1.42 min (method A). MS (ESI) (M+H)⁺ 591.21.

Biological Methods

There are a number of methods by which inhibitors of the BACE enzyme can be identified experimentally. The enzyme can be obtained from membrane samples from natural tissues or cultured cells or can be expressed recombinantly in a host cell by well known methods of molecular biology. The whole enzyme or a portion thereof can be expressed, for example, in bacterial, insect or mammalian cells to obtain a catalytically active enzyme species. The enzymatic activity and/or ligand binding capability of the enzyme can be assessed within these membrane samples, or the enzyme can be purified to varying extents. As an illustrative example, the nucleic acid sequence encoding the pro and catalytic domains of human BACE can be appended on the 5' end with an untranslated and signal sequence from the gene for acetylcholinesterase, and on the 3' end with a sequence encoding a poly-histidine tag. This cDNA can then be expressed in *Drosophila melanogaster* S2 cells in which the signal and pro sequences of the transcribed/translated protein are removed by cellular proteases and the catalytic domain, appended by a C-terminal poly-histidine tag, is secreted out into the cellular medium. The enzyme can then be purified from the culture medium by nickel affinity chromatography by methods well known to those trained in the art [Mallender, W. et al., "Characterization of recombinant, soluble beta-secretase from an insect cell expression system." *Mol. Pharmacol.* 2001, 59: 619-626]. Similar strategies for expressing and purifying various forms of BACE in bacterial, mammalian and other cell types would be known to one skilled in the art. A preferred method for determining the potency of a test compound in binding to the BACE enzyme is by monitoring the displacement of a suitable radioligand.

Radioligand displacement assays with a radiolabeled BACE inhibitor (WO 2004 013098, compound 3, where the methoxy group is substituted for C($^3$H)$_3$) were carried out using standard methods (Keen, M. (1999) in *Receptor Binding Techniques* (Walker, J. M. ed) p. 106 Humana Press, Totowa, N.J.). The HEK293-9B.A1 cell line, which overexpresses the BACE1 enzyme, was derived from HEK293 cells (Simmons, N. L. (1990) A cultured human renal epitheloid cell line responsive to vasoactive intestinal peptide. *Exp. Physiol.* 75:309-19.) by RAGE™ M (Harrington, J. J. et al. (2001) Creation of genome-wide protein expression libraries using random activation of gene expression. *Nat. Biotechnol.* 19:440-5; U.S. Pat. Nos. 6,410,266 and 6,361,972). T225 flask cultures of HEK293-9B.A1 were grown to 80% confluency in DMEM supplemented with 2 mM L-glutamine, 10 µg/ml penicillin, 10 µg/ml streptomycin, 3 µg/ml puromycin, 100 nM methotrexate, and 10% fetal bovine serum (Invitrogen, Carlsbad, Calif.), harvested, and resuspended at 2×10$^8$ cells per 10 ml of lysis buffer consisting of 50 mM HEPES pH 7.0 containing a protease inhibitor cocktail of AEBSF 104 µM, aprotinin 80 nM, leupeptin 2 µM, bestatin 4 µM, pepstatin A 1.5 µM, and E-64 1.4 µM (0.1% of protease inhibitor cocktail P8340, Sigma-Aldrich, St. Louis, Mo.) at 4° C. The resuspended cells were homogenized using a Polytron (Brinkman, Westbury, N.Y.) at setting 6 for 10 sec., then centrifuged at 48,000×g for 10 min. The resulting pellet was washed by repeating the resuspension, homogenization and centrifugation steps. The final pellet was resuspended in buffer at 4° C. to yield a total protein concentration of 5 mg/ml, then aliquots were frozen in liquid nitrogen for further storage at −70° C. Immediately before carrying out a binding assay, an aliquot of cell homogenate was thawed and diluted to a concentration of 100 µg/ml in assay buffer consisting of 50 mM HEPES pH 5.0 and 0.1% CHAPSO. Assays were initiated in polypropylene 96-well plates (Costar, Cambridge, Mass.) by the addition of 200 µl of cell homogenate to 50 µl of assay buffer containing 1 nM radioligand (WO 2004 013098, compound 3, where the methoxy group is substituted for C($^3$H)$_3$:80 Ci/mMol) and various concentrations of unlabelled compounds, and incubated for 1.5 hr. at 25° C. Separation of bound from free radioligand was by filtration on GFF glass fiber filters (Innotech Biosystems International, Lansing, Mich.) using an Innotech cell harvester. Filters were washed three times with 0.3 ml of phosphate buffered saline pH 7.0 at 4° C. and assessed for radioactivity using a Wallac 1450 Microbeta liquid scintillation counter (PerkinElmer, Boston, Mass.). Ki values of competing compounds were derived through Cheng-Prussoff correction of IC$_{50}$ values calculated using XLfit (IDBS, Guildford, UK).

Abbreviations

AEBSF: 4-(2-Aminoethyl)benzenesulfonyl fluoride hydrochloride

CHAPSO: 3-[(3-Cholamidopropyl)dimethylammonio]-2-hydroxy-1-propanesulfonate

D-MEM: Dulbecco's modified eagle medium

HEPES: 4-(2-Hydroxyethyl)piperazine-1-ethanesulfonic acid

RAGE™: Random Activation of Gene Expression™

The activity of specific compounds described herein and tested in the above assay is provided in Table 1.

TABLE 1

| Example No. | Activity Rating$^a$ |
|---|---|
| 1 | + |
| 2 | + |
| 3 | ++ |
| 4 | ++ |
| 5 | ++ |
| 6 | ++ |
| 7 | +++ |
| 8 | +++ |
| 9 | +++ |
| 10 | +++ |
| 11 | +++ |

$^a$Activity based on IC$_{50}$ values:
+++ = <5 nM
++ = 5-50 nM
+ = >50 nM

In Vitro Assay to Identify β-Secretase Inhibitor Based on the Inhibition of Aβ Formation from Membrane Preparations An isolated membrane fraction which contains functionally active β,β-secretase and β-APP substrates can generate β,β-secretase cleavage products including Aβ (Roberts, S. B.; Hendrick, J. P.; Vinitsky, A.; Lewis, M.; Smith, D. W.; Pak, R. PCT Publication WO 01/0175435; Fechteler, K.; Kostka, M.; Fuchs, M. Patent Application No. DE 99-19941039; Shearman, M.; Beher, D. et al., *Biochemistry,* 2000, 39, 8698-8704; Zhang, L. Song, L. et al., *Biochemistry* 2001, 40, 5049-5055). An isolated membrane fraction can be prepared from human derived cell lines such as HeLa and H4 which have been transfected with wild type or mutant forms of β-APP or a human alkaline phosphatase β-APP fusion construct, and stably express high levels of β-secretase substrates. The endogenous β-secretase present in the isolated membranes prepared at 0-4° C. cleaves the K-APP substrates when the membranes are shifted from 0-4 to 37° C. Detection of the cleavage products including Aβ can be monitored by standard techniques such as immunoprecipitation (Citron, M.; Diehl, T. S. et al., *Proc. Natl. Acad. Sci. USA,* 1996, 93, 13170-13175), western blot (Klafki, H.-W.; Ambramowski, D. et al., *J. Biol. Chem.* 1996, 271, 28655-28659), enzyme linked immunosorbent assay (ELISA) as demonstrated by Seubert, P.; Vigo-Pelfrey, C. et al., *Nature,* 1992, 359, 325-327, or by a preferred method using time-resolved fluorescence of the homogeneous sample containing membranes and Aβ (Roberts, S. B.; Hendrick, J. P.; Vinitsky, A.; Lewis, M.; Smith, D. W.; Pak, R. PCT Publication WO 01/0175435; Shearman, M.; Beher, D. et al., *Biochemistry*, 2000, 39, 8698-8704). The Aβ present in a homogeneous sample containing membranes can be detected by time-resolved fluorescence with two antibodies that recognize different epitopes of Aβ. One of the antibodies recognizes an epitope that is present in Aβ but not present in the precursor fragments; preferably the antibody binds the carboxyl terminus of Aβ generated by the β-secretase cleavage. The second antibody binds to any other epitope present on Aβ. For example, antibodies that bind the N-terminal region (e.g., 26D6-B2-B3® SIBIA Neurosciences, La Jolla, Calif.) or bind the C-terminal end (e.g., 953.2® antibody, Biosolutions, Newark, Del.) of the Aβ peptide are known. The antibodies are labeled with a pair of fluorescent adducts that transfer fluorescent energy when the adducts are brought in close proximity as a result of binding to the N- and C-terminal ends or regions of Aβ. A lack of fluorescence is indicative of the absence of cleavage products, resulting from inhibition of β-secretase. The isolated membrane assay can be used to identify candidate agents that inhibit the activity of β-secretase cleavage and Aβ production.

A typical membrane-based assay requires 45 μg membrane protein per well in a 96- or 384-well format. Membranes in a neutral buffer are combined with the test compound and shifted from 0-4 to 37° C. Test agents may typically consist of synthetic compounds, secondary metabolites from bacterial or fungal fermentation extracts, or extracts from plant or marine samples. All synthetic agents are initially screened at doses ranging from 10-100 μM or in the case of extracts at sufficient dilution to minimize cytotoxicity. Incubation of the membranes with the test agent will continue for approximately 90 minutes at which time fluorescence labeled antibodies are added to each well for Aβ quantitation. The time-resolved fluorescence detection and quantitation of Aβ is described elsewhere (Roberts, S. B.; Hendrick, J. P.; Vinitsky, A.; Lewis, M.; Smith, D. W.; Pak, R. PCT Publication WO 01/0175435; Shearman, M.; Beher, D. et al., *Biochemistry*, 2000. 39, 8698-8704). Results are obtained by analysis of the plate in a fluorescence plate reader and comparison to the mock treated membranes and samples in which known amounts of Aβ were added to construct a standard concentration curve. A positive acting compound is one that inhibits the Aβ relative to the control sample by at least 50% at the initial tested concentration. Compounds of the present application are considered active when tested in the above assay if the $IC_{50}$ value for the test compound is less than 50 μM. A preferred $IC_{50}$ value is less than 1 μM. A more preferred $IC_{50}$ value is less than 0.1 μM. If a compound is found to be active then a dose response experiment is performed to determine the lowest dose of compound necessary to elicit the inhibition of the production of Aβ.

In Vivo Assays for the Determination of Aβ Reduction by a β-Secretase Inhibitor

In vivo assays are available to demonstrate the inhibition of β-secretase activity. In these assays, animals, such as mice, that express normal levels of APP, β- and γ-secretase or are engineered to express higher levels of APP and hence Aβ can be used to demonstrate the utility of β-secretase inhibitors, as demonstrated with γ-secretase inhibitors [Dovey, H. et al., (2001), J. Neurochem. 76: 173-181]. In these assays, β-secretase inhibitors are administered to animals and Aβ levels in multiple compartments, such as plasma, cerebral spinal fluid, and brain extracts, are monitored for Aβ levels using methods previously outlined. For instance, Tg2576 mice, which over-express human APP, are administered β-secretase inhibitors by oral gavage at doses that will cause measurable Aβ lowering, typically less than 100 mg/kg. Three hours after dosing plasma, brain, and CSF are collected, frozen in liquid nitrogen, and stored at −80° C. until analysis. For Aβ detection, plasma is diluted 15-fold in PBS with 0.1% Chaps while CSF is diluted 15-fold in 1% Chaps with protease inhibitors (5 μg/ml leupeptin, 30 μg/ml aprotinin, 1 mM phenylmethylsulfonylfluoride, 1 μM pepstatin). Brains are homogenized in 1% Chaps with protease inhibitors using 24 ml solution/g brain tissue. Homogenates were then centrifuged at 100,000×g for 1 hr at 4° C. The resulting supernatants were then diluted 10-fold in 1% Chaps with protease inhibitors. Aβ levels in the plasma, CSF, and brain lysate can then be measured using time-resolved fluorescence of the homogenous sample or one of the other methods previously described.

A β-secretase inhibitor is considered active in one of the above in vivo assays if it reduces Aβ by at least 50% at a dosage of 100 mg/kg.

Dosage and Formulation

The compounds of the present application can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present application can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed to prevent or treat neurological disorders related to β-amyloid production or accumulation, such as Alzheimer's disease and Down's Syndrome.

The compounds of this application can be administered by any means that produces contact of the active agent with the agent's site of action in the body of a host, such as a human or a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present application will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

Advantageously, compounds of the present application may be administered in a single daily dose, or the total daily dosage may be administered in divided doses of two, three, or four times daily.

The compounds for the present application can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present application, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or β-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present disclosure can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present disclosure may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present disclosure may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

What is claimed is:

1. A compound of Formula (I); or a stereoisomer thereof

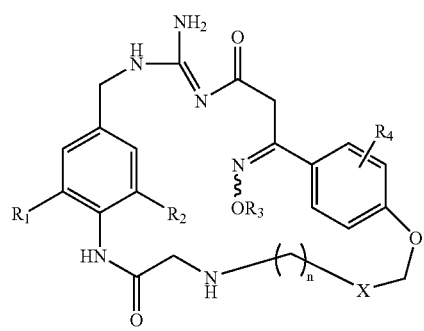

wherein
$R_1$ and $R_2$ are independently selected from hydrogen, $C_{1-4}$alkyl, halogen and $CF_3$;
$R_3$ is $C_{1-4}$alkyl, allyl, $C_{3-6}$cycloalkyl or $CF_3$;
$R_4$ is hydrogen, halogen, CN, $CF_3$, OH, —$NH_2$, $C_{1-6}$alkyl or $C_{1-6}$alkoxy;
n is an integer from 1 to 6; and
X is $(CH_2)_2$ or CH=CH;
or a nontoxic pharmaceutically acceptable salt thereof.

2. The compound of claim 1, wherein $R_4$ is H.
3. The compound of claim 2, wherein $R_1$ is Cl or Br.
4. The compound of claim 3, wherein $R_2$ is methyl, Cl or Br.
5. The compound of claim 4, wherein $R_3$ is methyl, ethyl or $CF_3$.
6. The compound of claim 5, wherein n is 3 or 4.
7. The compound according to claim 1 selected from the group consisting of:
   Isomer A of 4-amino-23,26-dichloro-13-oxa-3,5,18,21-tetraazatricyclo[20.2.2.2$^{9,12}$]octacosa-1(24),4,9,11,15,22,25,27-octaene-6,8,20-trione 8-(O-ethyloxime);
   Isomer B of 4-amino-23,26-dichloro-13-oxa-3,5,18,21-tetraazatricyclo-[20.2.2.2$^{9,12}$]octacosa-1(24),4,9,11,15,22,25,27-octaene-6,8,20-trione 8-(O-ethyloxime);
   4-Amino-23,26-dichloro-13-oxa-3,5,18,21-tetraazatricyclo[20.2.2.2$^{9,12}$]-octacosa-1 (24),4,9,11,22,25,27-heptaene-6,8,20-trione 8-(O-ethyloxime);

Isomer A of 4-amino-24,27-dichloro-13-oxa-3,5,19,22-tetraazatricyclo-[21.2.2.29,12]nonacosa-1(25),4,9,11,15,23,26,28-octaene-6,8,21-trione 8-(O-ethyloxime);

Isomer B of 4-amino-24,27-dichloro-13-oxa-3,5,19,22-tetraazatricyclo-[21.2.2.29,12]nonacosa-1(25)-4,9,11,15,23,26,28-octaene-6,8,21-trione 8-(O-ethyloxime);

4-Amino-24,27-dichloro-13-oxa-3,5,19,22-tetraazatricyclo[21.2.2.2$^{9,12}$]-nonacosa-1(25),4,9, 11,23,26,28-heptaene-6,8,21-trione 8-(O-ethyloxime;

Isomer A of 4-amino-25,28-dichloro-13-oxa-3,5,20,23-tetraazatricyclo[22.2.2.29,12]triaconta-1(26),4,9,11,15,24,27,29-octaene-6,8,22-trione 8-(O-ethyloxime);

Isomer B of 4-amino-25,28-dichloro-13-oxa-3,5,20,23-tetraazatricyclo-[22.2.2.29,12]triaconta-1(26),4,9,11,15,24,27,29-octaene-6,8,22-trione 8-(O-ethyloxime);

4-Amino-25,28-dichloro-13-oxa-3,5,20,23-tetraazatricyclo[22.2.2.2$^{9,12}$]-triaconta-1(26),4,9, 11,24,27,29-heptaene-6,8,22-trione 8-(O-ethyloxime);

4-Amino-26,29-dichloro-13-oxa-3,5,21,24-tetraazatricyclo-[23.2.2.2$^{9,12}$]hentriaconta-1(27),4,9,11,15,25,28,30-octaene-6,8,23-trione 8-(O-ethyloxime); and 4-Amino-26,29-dichloro-13-oxa-3,5,21,24-tetraazatricyclo-[23.2.2.2$^{9,12}$]hentriaconta-1(27),4 ,9, 11,25,28,30-heptaene-6,8,23-trione 8-(O-ethyloxime);

or a nontoxic pharmaceutically acceptable salt thereof.

8. A pharmaceutical composition comprising a therapeutically effective amount of a compound of claim 1 in association with a pharmaceutically acceptable adjuvant, carrier or diluent.

* * * * *